United States Patent
Benson et al.

(10) Patent No.: US 7,807,414 B2
(45) Date of Patent: Oct. 5, 2010

(54) ANTI-IL-23 ANTIBODIES, COMPOSITIONS, METHODS AND USES

(75) Inventors: Jacqueline Benson, Malvern, PA (US); Mark Cunningham, Kennett Square, PA (US); Cynthia Duchala, North Wales, PA (US); Jill M. Giles-Komar, Dowingtown, PA (US); Jinquan Luo, Malvern, PA (US); Michael A. Rycyzyn, Berwyn, PA (US); Sweet Raymond, Bala Cynwyd, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 47 days.

(21) Appl. No.: 12/370,872

(22) Filed: Feb. 13, 2009

(65) Prior Publication Data

US 2009/0162371 A1 Jun. 25, 2009

Related U.S. Application Data

(62) Division of application No. 11/479,464, filed on Jun. 30, 2006, now Pat. No. 7,491,391.

(60) Provisional application No. 60/695,831, filed on Jun. 30, 2005.

(51) Int. Cl.
  *C12N 5/10* (2006.01)
  *C12N 15/13* (2006.01)
  *C12N 15/63* (2006.01)
(52) U.S. Cl. ............... 435/69.6; 536/23.53; 435/325; 435/320.1; 435/252.3
(58) Field of Classification Search ............... None
  See application file for complete search history.

(56) References Cited

U.S. PATENT DOCUMENTS

| | | | |
|---|---|---|---|
| 6,060,284 A | 5/2000 | Bazan | |
| 6,479,634 B1 | 11/2002 | Bazan | |
| 6,495,667 B1 | 12/2002 | Bazan | |
| 6,610,285 B1 | 8/2003 | Hirata | |
| 6,632,927 B2 | 10/2003 | Adair et al. | |
| 6,756,481 B2 | 6/2004 | Chirica et al. | |
| 6,800,460 B1 | 10/2004 | Oppmann et al. | |
| 6,835,825 B1 | 12/2004 | Bazan | |
| RE39,015 E | 3/2006 | Bazan et al. | |
| 7,090,847 B1 | 8/2006 | Oppmann et al. | |
| 7,183,382 B2 | 2/2007 | Oppmann et al. | |
| 7,247,711 B2 | 7/2007 | Benson et al. | |
| 7,252,971 B2 | 8/2007 | Benson et al. | |
| 7,282,204 B2 | 10/2007 | Oft et al. | |
| 2003/0162261 A1 | 8/2003 | Oppmann et al. | |
| 2004/0258686 A1 | 12/2004 | Chirica et al. | |
| 2005/0208052 A1 | 9/2005 | Katsikis et al. | |
| 2005/0244874 A1 | 11/2005 | Kastelein et al. | |
| 2007/0048315 A1 | 3/2007 | Presta | |

FOREIGN PATENT DOCUMENTS

| | | |
|---|---|---|
| WO | WO 99/05280 A1 | 2/1999 |
| WO | WO 99/40195 A1 | 8/1999 |
| WO | WO 00/09552 A1 | 2/2000 |
| WO | WO 00/53631 A1 | 9/2000 |
| WO | WO 00/70049 A2 | 11/2000 |
| WO | WO 01/18051 A2 | 3/2001 |
| WO | WO 01/85790 A2 | 11/2001 |
| WO | WO 2004/042009 A2 | 5/2004 |
| WO | WO 2004/058178 A2 | 7/2004 |
| WO | WO 2004/071517 A2 | 8/2004 |
| WO | WO 2004/081190 A2 | 9/2004 |
| WO | WO 2004/101750 A2 | 11/2004 |
| WO | WO 2007/024846 A2 | 3/2007 |

OTHER PUBLICATIONS

Oppmann, et al., "Novel p19 Protein Engages IL-12p40 to Form a Cytokine, IL-23, with Biological Activities Similar as Well as Distinct from IL-12," Immunity, 13: 715-725 (2000).
Peter J. Barnes, "Cytokine-directed therapies for the treatment of chronic airway diseases," Cytokine & Growth Factor Reviews 14 (2003): 511-522 (2003).
Trinchieri, et al., "The IL-12 Family of Heterodimeric Cytokines: New Players in the Regulation of T Cell Responses," Immunity, 19: 641-644 (2003).
Maguire van Seventer, et al., "Interferon-β differentially regulates expression of the IL-12 family members p35, p40, p19 and EB13 in activated human dendritic cells," Journal of Neuroimmunology, 133: 60-71 (2002).
Yadav, et al., "Cytokines and autoimmunity: redundancy defines their complex nature," Current Opinion in Immunology, 15: 697-703 (2003).
Murphy, et al., "Divergent Pro- and Antiinflammatory Roles for IL-23 and IL-12 in Joint Autoimmune Inflammation," Journal of Experimental Medicine, 198(12): 1951-1957 (2003).
David M. Frucht, "IL-23: A Cytokine That Acts on Memory T Cells," Science STKE, 114: 1-3 (2002).
Wiekowski, et al., "Ubiquitous Transgenic Expression of the IL-23 Subunit p19 Induces Multiorgan Inflammation, Runting, Infertility, and Premature Death," Journal of Immunology, 166: 7563-7570(2001).
Belladonna, et al., "IL-23 and IL-12 Have Overlapping, but Distinct, Effects on Murine Dendritic Cells," The Journal of Immunology, 168: 5448-5454 (2002).
Parham, et al., "A Receptor for the Heterodimeric Cytokine IL-23 is Composed of IL-12Rβ1 and a Novel Cytokine Receptor Subunit, IL-23R," The Journal of Immunology, 168: 5699-5708 (2002).
Cua, et al., "Interleukin-23 rather than interleukin-12 is the critical cytokine for autoimmune inflammation of the brain," Nature, 421: 744-748 (2003).
GenBank Accession No. AF301620, Oppmann, et al., Dec. 4, 2000.

(Continued)

*Primary Examiner*—Prema Mertz
(74) *Attorney, Agent, or Firm*—Eric A. Dichter

(57) ABSTRACT

An anti-IL-23p19 antibody, including isolated nucleic acids that encode at least one anti-IL-23p19 antibody, vectors, host cells, transgenic animals or plants, and methods of making and using thereof have applications in diagnostic and/or therapeutic compositions, methods and devices.

12 Claims, 10 Drawing Sheets

OTHER PUBLICATIONS

GenBank Accession No. AA418955, Hillier, et al., May 12, 1997.
GenBank Accession No. C06368, J. Takeda, Aug. 9, 1996.
GenBank Accession No. AA418747, Hillier, et al., May 12, 1997.
PCT International Search Report dated Sep. 5, 2007.
Panka, et al., "Variable region framework differences result in decreased or increased affinity of variant anti-digoxin antibodies," Proceedings of the National Academy of Sciences USA, 85: 3080-3084 (1988).
Rudikoff, et al., "Single amino acid substitution altering antigen-binding specificity," Proceedings of the National Academy of Science USA, 79: 1979-1983 (1982).
Amit, et al., Three-Dimensional Structure of an Antigen-Antibody Complex at 2.8 A Resolution, Science, 233(4765):747-753 (1986).
Sehy, et al., "Unambiguous Detection of IL-23 (p19/p40) Protein in Native Samples Using a Novel Enzyme-Linked Immunosorbent Assay," FASEB Journal, 19(4): A945-A946 (2005).
Supplementary European Search Report dated Jul. 20, 2009.

SEQUENCE LISTING

<160> NUMBER OF SEQ ID NOS: 41

<210> SEQ ID NO 1
<211> LENGTH: 189
<212> TYPE: PRT
<213> ORGANISM: Homo sapiens

<400> SEQUENCE: 1

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Ala Gln Leu His Ala Ser Leu
        115                 120                 125

Leu Gly Leu Ser Gln Leu Leu Gln Pro Glu Gly His His Trp Gln Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 2
<211> LENGTH: 450
<212> TYPE: DNA
<213> ORGANISM: Homo sapiens

<400> SEQUENCE: 2

```
atgagcagtg aacacagacc cctcaccatg aacttcgggc tcagattgat tttccttgtc      60
cttactttaa aggtgtcca gtgtgacgtg aacttggtgg agtctggggg aggcttagtg      120
aagcctggag ggtccctgaa actctcctgt gcagcctctg gattcacttt cagtagctat      180
accatgtctt gggttcgcca gactccggag aagaggctgg agtgggtcgc aaccattagt      240
agtggtggta cttacaccta ctatccagac agtgtgaagg gccgattcac catctccaga      300
gacaatgcca agaacaccct gtacctgcaa atgagcagtc tgaagtctga ggacacagcc      360
atgttttact gtacaagaga taaccatgct tacgacaggg gcccttcctt tgactactgg      420
ggccaaggcg ccactctcac agtctcctca                                       450
```

<210> SEQ ID NO 3
<211> LENGTH: 150
<212> TYPE: PRT
<213> ORGANISM: Homo sapiens

<400> SEQUENCE: 3

Met Ser Ser Glu His Arg Pro Leu Thr Met Asn Phe Gly Leu Arg Leu
1               5                   10                  15

Ile Phe Leu Val Leu Thr Leu Lys Gly Val Gln Cys Asp Val Asn Leu
            20                  25                  30

Val Glu Ser Gly Gly Gly Leu Val Lys Pro Gly Gly Ser Leu Lys Leu
        35                  40                  45

Ser Cys Ala Ala Ser Gly Phe Thr Phe Ser Ser Tyr Thr Met Ser Trp
    50                  55                  60

Val Arg Gln Thr Pro Glu Lys Arg Leu Glu Trp Val Ala Thr Ile Ser
65                  70                  75                  80

Ser Gly Gly Thr Tyr Thr Tyr Tyr Pro Asp Ser Val Lys Gly Arg Phe
                85                  90                  95

Thr Ile Ser Arg Asp Asn Ala Lys Asn Thr Leu Tyr Leu Gln Met Ser
            100                 105                 110

Ser Leu Lys Ser Glu Asp Thr Ala Met Phe Tyr Cys Thr Arg Asp Asn
        115                 120                 125

His Ala Tyr Asp Arg Gly Pro Phe Phe Asp Tyr Trp Gly Gln Gly Ala
    130                 135                 140

Thr Leu Thr Val Ser Ser
145                 150

<210> SEQ ID NO 4
<211> LENGTH: 10
<212> TYPE: PRT
<213> ORGANISM: Homo sapiens

<400> SEQUENCE: 4

Gly Phe Thr Phe Ser Ser Tyr Thr Met Ser
1               5                   10

<210> SEQ ID NO 5
<211> LENGTH: 17
<212> TYPE: PRT
<213> ORGANISM: Homo sapiens

```
<400> SEQUENCE: 5

Thr Ile Ser Ser Gly Gly Thr Tyr Thr Tyr Tyr Pro Asp Ser Val Lys
1               5                   10                  15
Gly

<210> SEQ ID NO 6
<211> LENGTH: 13
<212> TYPE: PRT
<213> ORGANISM: Homo sapiens

<400> SEQUENCE: 6

Asp Asn His Ala Tyr Asp Arg Gly Pro Phe Phe Asp Tyr
1               5                   10

<210> SEQ ID NO 7
<211> LENGTH: 399
<212> TYPE: DNA
<213> ORGANISM: Homo sapiens

<400> SEQUENCE: 7
atggattcac aggcccaggt tcttttgtta ctgctgctat gggtttctgg tacctgtggg      60
gacattgtga tgtcacagtc cccatcctcc ctagttgtgt cagttggaga gaaggttact    120
atgagctgca gtccagtcaa gaacctcttt tataggagta atcaaaagaa ccacttggcc    180
tggtaccagc agaaaccagg gcagtctcct acactgctga tttactggac gtccactagg    240
gaatctgggg tccctgatcg cttcacaggc agtggatctg gacagatttt cactctcacc    300
atcagccgtg tgaaggctga agacctggca gtttattact gtcagcaata ttatagctat    360
cctccgacgt tcggtggagg caccaagctg gaaatcaaa                           399

<210> SEQ ID NO 8
<211> LENGTH: 133
<212> TYPE: PRT
<213> ORGANISM: Homo sapiens

<400> SEQUENCE: 8

Met Asp Ser Gln Ala Gln Val Leu Leu Leu Leu Leu Leu Trp Val Ser
1               5                   10                  15

Gly Thr Cys Gly Asp Ile Val Met Ser Gln Ser Pro Ser Ser Leu Val
                20                  25                  30

Val Ser Val Gly Glu Lys Val Thr Met Ser Cys Lys Ser Ser Gln Asn
            35                  40                  45

Leu Phe Tyr Arg Ser Asn Gln Lys Asn His Leu Ala Trp Tyr Gln Gln
        50                  55                  60

Lys Pro Gly Gln Ser Pro Thr Leu Leu Ile Tyr Trp Thr Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Arg Val Lys Ala Glu Asp Leu Ala Val Tyr
            100                 105                 110

Tyr Cys Gln Gln Tyr Tyr Ser Tyr Pro Pro Thr Phe Gly Gly Gly Thr
        115                 120                 125

Lys Leu Glu Ile Lys
        130
```

```
<210> SEQ ID NO 9
<211> LENGTH: 17
<212> TYPE: PRT
<213> ORGANISM: Homo sapiens

<400> SEQUENCE: 9

Lys Ser Ser Gln Asn Leu Phe Tyr Arg Ser Asn Gln Lys Asn His Leu
1               5                   10                  15
Ala

<210> SEQ ID NO 10
<211> LENGTH: 7
<212> TYPE: PRT
<213> ORGANISM: Homo sapiens

<400> SEQUENCE: 10

Trp Thr Ser Thr Arg Glu Ser
1               5

<210> SEQ ID NO 11
<211> LENGTH: 9
<212> TYPE: PRT
<213> ORGANISM: Homo sapiens

<400> SEQUENCE: 11

Gln Gln Tyr Tyr Ser Tyr Pro Pro Thr
1               5

<210> SEQ ID NO 12
<211> LENGTH: 450
<212> TYPE: DNA
<213> ORGANISM: Homo sapiens

<400> SEQUENCE: 12
atgagcagtg aacacagacc cctcaccatg aacttcgggc tcagattgat tttccttgtc     60
ctgactttaa aaggtgtcca gtgtgacgtg aacttggtgg agtctggggg aggcttagtg    120
aagcctggag ggtccctgaa actctcctgt gcagcctctg gattcacttt cagtagctat    180
accatgtctt gggttcgcca gactccggag aagaggctgg agtgggtcgc aaccattagt    240
agtggtggta cttacaccta ctatccagac agtgtgaagg gccgattcac catttccaga    300
gacaatgcca agaatacatt gtatctgcaa atgagcagtc tgaagtctga ggacacagcc    360
atctttattg gtacaagaga taaccatgct tacgacaggg gccctttctt tgactcctgg    420
ggccaaggcg ccactctcac agtctcctca                                     450

<210> SEQ ID NO 13
<211> LENGTH: 150
<212> TYPE: PRT
<213> ORGANISM: Homo sapiens

<400> SEQUENCE: 13

Met Ser Ser Glu His Arg Pro Leu Thr Met Asn Phe Gly Leu Arg Leu
1               5                   10                  15

Ile Phe Leu Val Leu Thr Leu Lys Gly Val Gln Cys Asp Val Asn Leu
            20                  25                  30

Val Glu Ser Gly Gly Gly Leu Val Lys Pro Gly Gly Ser Leu Lys Leu
        35                  40                  45

Ser Cys Ala Ala Ser Gly Phe Thr Phe Ser Ser Tyr Thr Met Ser Trp
    50                  55                  60
```

Val Arg Gln Thr Pro Glu Lys Arg Leu Glu Trp Val Ala Thr Ile Ser
65                  70                  75                  80

Ser Gly Gly Thr Tyr Thr Tyr Tyr Pro Asp Ser Val Lys Gly Arg Phe
            85                  90                  95

Thr Ile Ser Arg Asp Asn Ala Lys Asn Thr Leu Tyr Leu Gln Met Ser
            100                 105                 110

Ser Leu Lys Ser Glu Asp Thr Ala Ile Phe Tyr Cys Thr Arg Asp Asn
        115                 120                 125

His Ala Tyr Asp Arg Gly Pro Phe Phe Asp Ser Trp Gly Gln Gly Ala
    130                 135                 140

Thr Leu Thr Val Ser Ser
145             150

<210> SEQ ID NO 14
<211> LENGTH: 10
<212> TYPE: PRT
<213> ORGANISM: Homo sapiens

<400> SEQUENCE: 14

Gly Phe Thr Phe Ser Ser Tyr Thr Met Ser
1               5                   10

<210> SEQ ID NO 15
<211> LENGTH: 16
<212> TYPE: PRT
<213> ORGANISM: Homo sapiens

<400> SEQUENCE: 15

Ile Ser Ser Gly Gly Thr Tyr Thr Tyr Tyr Pro Asp Ser Val Lys Gly
1               5                   10                  15

<210> SEQ ID NO 16
<211> LENGTH: 13
<212> TYPE: PRT
<213> ORGANISM: Homo sapiens

<400> SEQUENCE: 16

Asp Asn His Ala Tyr Asp Arg Gly Pro Phe Phe Asp Ser
1               5                   10

<210> SEQ ID NO 17
<211> LENGTH: 399
<212> TYPE: DNA
<213> ORGANISM: Homo sapiens

<400> SEQUENCE: 17
atggattcac aggcccaggt tcttatgtta ctgctgctat gggtttctgg tacctgtggg    60
gacattgtga tgtcacagtc tccatcctcc ctagctgtgt cagttggaga aaggttact    120 atgagctgca agtccagtca gaacctcttt tataggaata tcaaaagaa ctacttggcc    180 tggtaccagc agaaaccagg gcagtctcct acactgctga tttactggac gtccactagg    240
gagtctgggg tccctgatcg cttcacaggc agtggatctg ggacagattt cactctcacc    300
atcagccgtg tgaaggctga agacctggca gtttattact gtcagcaata ttatagctat    360
cctccgacgt tcggtggagg caccaagctg gaaatcaaa                          399

<210> SEQ ID NO 18
<211> LENGTH: 133
<212> TYPE: PRT
<213> ORGANISM: Homo sapiens -continued

```
<400> SEQUENCE: 18

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Asn
        35                  40                  45

Leu Phe Tyr Arg Asn Asn Gln Lys Asn Tyr Leu Ala Trp Tyr Gln Gln
    50                  55                  60

Lys Pro Gly Gln Ser Pro Thr Leu Leu Ile Tyr Trp Thr Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Arg Val Lys Ala Glu Asp Leu Ala Val Tyr
            100                 105                 110

Tyr Cys Gln Gln Tyr Tyr Ser Tyr Pro Pro Thr Phe Gly Gly Gly Thr
        115                 120                 125

Lys Leu Glu Ile Lys
    130

<210> SEQ ID NO 19
<211> LENGTH: 17
<212> TYPE: PRT
<213> ORGANISM: Homo sapiens

<400> SEQUENCE: 19

Lys Ser Ser Gln Asn Leu Phe Tyr Arg Asn Asn Gln Lys Asn Tyr Leu
1               5                   10                  15

Ala

<210> SEQ ID NO 20
<211> LENGTH: 8
<212> TYPE: PRT
<213> ORGANISM: Homo sapiens

<400> SEQUENCE: 20

Tyr Trp Thr Ser Thr Arg Glu Ser
1               5

<210> SEQ ID NO 21
<211> LENGTH: 9
<212> TYPE: PRT
<213> ORGANISM: Homo sapiens

<400> SEQUENCE: 21

Gln Gln Tyr Tyr Ser Tyr Pro Pro Thr
1               5

<210> SEQ ID NO 22
<211> LENGTH: 426
<212> TYPE: DNA
<213> ORGANISM: Homo sapiens

<400> SEQUENCE: 22
atgtacttgg gactgaactg tgtattcata gttttctctc taaaaggtgt ccagagtgaa      60
gtgaaccttg aggagtctgg aggaggcttg gtgcaacctg gaagatccat gaaactctcc    120
tgtgttgcct ctggattcac tttcagtaac tactggatga cctgggtccg ccagtctcca    180
gagaaggggc ttgagtgggt tgctgaaatt agattgaaat ctaataatta tgcaacacat    240
```

```
tatgcggagt ctgtgaaagg gaggttcacc atctcaagag atgattccaa aagtagtgtc    300
tacctgcaaa tgaacaactt aagagctgaa gacactgcca tttattactg taccagggg     360 gggggttacg acgtaggagc ctggtttgct tactggggcc aagggactct ggtcactgtc    420
tctgca                                                               426
```

```
<210> SEQ ID NO 23
<211> LENGTH: 142
<212> TYPE: PRT
<213> ORGANISM: Homo sapiens

<400> SEQUENCE: 23

Met Tyr Leu Gly Leu Asn Cys Val Phe Ile Val Phe Leu Leu Lys Gly
1               5                   10                  15

Val Gln Ser Glu Val Asn Leu Glu Glu Ser Gly Gly Gly Leu Val Gln
            20                  25                  30

Pro Gly Arg Ser Met Lys Leu Ser Cys Val Ala Ser Gly Phe Thr Phe
        35                  40                  45

Ser Asn Tyr Trp Met Thr Trp Val Arg Gln Ser Pro Glu Lys Gly Leu
    50                  55                  60

Glu Trp Val Ala Glu Ile Arg Leu Lys Ser Asn Asn Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Ala Ile Tyr Tyr Cys Thr Arg Gly Gly Gly Tyr Asp Val Gly Ala Trp
        115                 120                 125

Phe Ala Tyr Trp Gly Gln Gly Thr Leu Val Thr Val Ser Ala
    130                 135                 140

<210> SEQ ID NO 24
<211> LENGTH: 10
<212> TYPE: PRT
<213> ORGANISM: Homo sapiens

<400> SEQUENCE: 24

Gly Phe Thr Phe Ser Asn Tyr Trp Met Thr
1               5                   10

<210> SEQ ID NO 25
<211> LENGTH: 19
<212> TYPE: PRT
<213> ORGANISM: Homo sapiens

<400> SEQUENCE: 25

Glu Ile Arg Leu Lys Ser Asn Asn Tyr Ala Thr His Tyr Ala Glu Ser
1               5                   10                  15

Val Lys Gly

<210> SEQ ID NO 26
<211> LENGTH: 12
<212> TYPE: PRT
<213> ORGANISM: Homo sapiens

<400> SEQUENCE: 26

Gly Gly Gly Tyr Asp Val Gly Ala Trp Phe Ala Tyr
1               5                   10
```

```
<210> SEQ ID NO 27
<211> LENGTH: 393
<212> TYPE: DNA
<213> ORGANISM: Homo sapiens

<400> SEQUENCE: 27
atggagtcag acacactcct gctatgggtg ctgctgctct gggttccagg ctccactggt      60
gacattgtgc tcacccaatc tccagcttct ttggctgtgt ctctagggca gagagccacc     120
atctcctgca gagccagtga aaatgttgaa tattatggca caggtttaat tcagtggtac     180
caacagaaac caggacagcc acccaaactc ctcatctatg cttcatccaa cgtagaatct     240
ggggtccctg ccaggtttag tggcagtggg tctgggacag acttcagcct ctacatccat     300
cctgtggagg aggatgatat tgcaatgtat ttctgtcagc aaagtaggaa ggttccttcg     360
acgttcggtg gaggcaccaa gctggaaatc aaa                                  393

<210> SEQ ID NO 28
<211> LENGTH: 131
<212> TYPE: PRT
<213> ORGANISM: Homo sapiens

<400> SEQUENCE: 28

Met Glu Ser Asp Thr Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Asn
        35                  40                  45

Val Glu Tyr Tyr Gly Thr Gly Leu Ile Gln Trp Tyr Gln Gln Lys Pro
    50                  55                  60

Gly Gln Pro Pro Lys Leu Leu Ile Tyr Ala Ser Ser Asn Val Glu Ser
65                  70                  75                  80

Gly Val Pro Ala Arg Phe Ser Gly Ser Gly Ser Gly Thr Asp Phe Ser
                85                  90                  95

Leu Tyr Ile His Pro Val Glu Glu Asp Asp Ile Ala Met Tyr Phe Cys
            100                 105                 110

Gln Gln Ser Arg Lys Val Pro Ser Thr Phe Gly Gly Gly Thr Lys Leu
        115                 120                 125

Glu Ile Lys
    130

<210> SEQ ID NO 29
<211> LENGTH: 15
<212> TYPE: PRT
<213> ORGANISM: Homo sapiens

<400> SEQUENCE: 29

Arg Ala Ser Glu Asn Val Glu Tyr Tyr Gly Thr Gly Leu Ile Gln
1               5                   10                  15

<210> SEQ ID NO 30
<211> LENGTH: 7
<212> TYPE: PRT
<213> ORGANISM: Homo sapiens

<400> SEQUENCE: 30

Ala Ser Ser Asn Val Glu Ser
1               5
```

<210> SEQ ID NO 31
<211> LENGTH: 9
<212> TYPE: PRT
<213> ORGANISM: Homo sapiens

<400> SEQUENCE: 31

Gln Gln Ser Arg Lys Val Pro Ser Thr
1               5

<210> SEQ ID NO 32
<211> LENGTH: 417
<212> TYPE: DNA
<213> ORGANISM: Homo sapiens

<400> SEQUENCE: 32

```
atggtgttgg ggctgaagtg ggttttcttt gttgtttttt atcaaggtgt gcattgtgag    60
gtgcaacttg ttgagtctgg tggaggattg gtgcagccta aaggatcatt gaaactctca   120
tgtgccgcct ctggtttcaa cttcaatacc tatgccatgc actgggtctg ccaggctcca   180
ggaaagggtt tggaatggat tggtcgcata agaagtaaaa gtcataatta tgcaacagac   240
tatgccgatc cagtgaaaga cagattcacc atctccagag atgattcaca aggcttgctc   300
tatctgctaa tgaacaacct gaaaactgag gacacagcca tgtattactg tatgagggag   360
ggaatctatg gtagttttgc ttactggggc caagggactc tggtcactgt ctctgca      417
```

<210> SEQ ID NO 33
<211> LENGTH: 139
<212> TYPE: PRT
<213> ORGANISM: Homo sapiens

<400> SEQUENCE: 33

Met Val Leu Gly Leu Lys Trp Val Phe Phe Val Val Phe Tyr Gln Gly
1               5                   10                  15
Val His Cys Glu Val Gln Leu Val Glu Ser Gly Gly Gly Leu Val Gln
                20                  25                  30
Pro Lys Gly Ser Leu Lys Leu Ser Cys Ala Ala Ser Gly Phe Asn Phe
            35                  40                  45
Asn Thr Tyr Ala Met His Trp Val Cys Gln Ala Pro Gly Lys Gly Leu
        50                  55                  60
Glu Trp Ile Gly Arg Ile Arg Ser Lys Ser His Asn Tyr Ala Thr Asp
65                  70                  75                  80
Tyr Ala Asp Pro Val Lys Asp Arg Phe Thr Ile Ser Arg Asp Asp Ser
                85                  90                  95
Gln Gly Leu Leu Tyr Leu Leu Met Asn Asn Leu Lys Thr Glu Asp Thr
            100                 105                 110
Ala Met Tyr Tyr Cys Met Arg Glu Gly Ile Tyr Gly Ser Phe Ala Tyr
        115                 120                 125
Trp Gly Gln Gly Thr Leu Val Thr Val Ser Ala
    130                 135

<210> SEQ ID NO 34
<211> LENGTH: 10
<212> TYPE: PRT
<213> ORGANISM: Homo sapiens

<400> SEQUENCE: 34

Gly Phe Asn Phe Asn Thr Tyr Ala Met His
1               5                   10

<210> SEQ ID NO 35
<211> LENGTH: 18
<212> TYPE: PRT
<213> ORGANISM: Homo sapiens

<400> SEQUENCE: 35

Ile Arg Ser Lys Ser His Asn Tyr Ala Thr Asp Tyr Ala Asp Pro Val
1               5                   10                  15

Lys Asp

<210> SEQ ID NO 36
<211> LENGTH: 9
<212> TYPE: PRT
<213> ORGANISM: Homo sapiens

<400> SEQUENCE: 36

Glu Gly Ile Tyr Gly Ser Phe Ala Tyr
1               5

<210> SEQ ID NO 37
<211> LENGTH: 393
<212> TYPE: DNA
<213> ORGANISM: Homo sapiens

<400> SEQUENCE: 37

```
atggagacag acacactcct gttatgggta ctgctgctct gggttccagg ttccactggt    60
gacattgtgc tgacacagtc tcctgcttcc ttagctgtat ctctggggca gagggccacc   120
atctcatgca gggccagcaa aagtgtcagt tcatctgcct atagtttttt ccactggtac   180
caacagaagc caggacagcc acccaaactc ctcatctatc ttgcatccaa cctacaatct   240
ggggtccctg ccaggttcag tggcagtggg tctgggacag acttcaccct caacatccat   300
cctgtggagg cggaggatgc tgcaacctat tactgtcaac acagtgggga gcttccattc   360
acgttcggct cggggacaaa gttggaaata aaa                                393
```

<210> SEQ ID NO 38
<211> LENGTH: 131
<212> TYPE: PRT
<213> ORGANISM: Homo sapiens

<400> SEQUENCE: 38

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Ser Ala Tyr Ser Phe Phe His Trp Tyr Gln Gln Lys Pro
    50                  55                  60

Gly Gln Pro Pro Lys Leu Leu Ile Tyr Leu Ala Ser Asn Leu Gln Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Ala Glu Asp Ala Ala Thr Tyr Tyr Cys
            100                 105                 110

Gln His Ser Gly Glu Leu Pro Phe Thr Phe Gly Ser Gly Thr Lys Leu
        115                 120                 125

Glu Ile Lys
        130

```
<210> SEQ ID NO 39
<211> LENGTH: 16
<212> TYPE: PRT
<213> ORGANISM: Homo sapiens

<400> SEQUENCE: 39

Cys Arg Ala Ser Lys Ser Val Ser Ser Ser Ala Tyr Ser Phe Phe His
1               5                   10                  15

<210> SEQ ID NO 40
<211> LENGTH: 7
<212> TYPE: PRT
<213> ORGANISM: Homo sapiens

<400> SEQUENCE: 40

Leu Ala Ser Asn Leu Gln Ser
1               5

<210> SEQ ID NO 41
<211> LENGTH: 10
<212> TYPE: PRT
<213> ORGANISM: Homo sapiens

<400> SEQUENCE: 41

Cys Gln His Ser Gly Glu Leu Pro Phe Thr
1               5                   10
```

ANTI-IL-23 ANTIBODIES, COMPOSITIONS, METHODS AND USES

CROSS-REFERENCE TO RELATED APPLICATION

This application is a divisional of application Ser. No. 11/479,464, filed 30 Jun. 2006, now U.S. Pat. No. 7,491,391 now allowed, which claims the benefit of U.S. Provisional Application Ser. No. 60/695,831, filed 30 Jun. 2005, the entire contents of which is incorporated herein by reference.

FIELD OF THE INVENTION

The present invention relates to antibodies, including specified portions or variants, specific for at least one IL-23 protein or fragment thereof, as well as anti-idiotype antibodies, and nucleic acids encoding anti-IL-23p19 antibodies, complementary nucleic acids, vectors, host cells, and methods of making and using thereof, including therapeutic formulations, administration and devices.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Recent studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

SUMMARY OF THE INVENTION

The present invention provides isolated mammalian, including, without limitation, human, antibodies that bind to the p19 subunit of IL-23, anti-IL-23p19 antibodies (also referred to as IL-23p19 antibodies), immunoglobulins, fragments, cleavage products and other specified portions and variants thereof, as well as anti-IL-23p19 antibody compositions, IL-23p19 anti-idiotype antibodies, encoding or complementary nucleic acids, vectors, host cells, compositions, combinations, formulations, devices, transgenic animals, transgenic plants, and methods of making and using them.

The present invention provides, in one aspect, isolated nucleic acid molecules comprising, complementary, or hybridizing to, a polynucleotide encoding specific anti-IL-23p19 antibodies or anti-idiotype antibodies, comprising at least one specified sequence, domain, portion or variant thereof. The present invention further provides recombinant vectors comprising said anti-IL-23p19 antibody nucleic acid molecules, host cells containing such nucleic acids and/or recombinant vectors, as well as methods of making and/or using such antibody nucleic acids, vectors and/or host cells.

The present invention also provides at least one method for expressing at least one anti-IL-23p19 antibody, or IL-23p19 anti-idiotype antibody, in a host cell, comprising culturing a host cell as described herein under conditions wherein at least one anti-IL-23p19 antibody is expressed in detectable and/or recoverable amounts.

The present invention also provides at least one composition comprising (a) an isolated anti-IL-23p19 antibody encoding nucleic acid and/or antibody as described herein; and (b) a suitable and/or pharmaceutically acceptable carrier or diluent.

The present invention further provides at least one anti-IL-23p19 antibody method or composition, for administering a therapeutically effective amount to modulate or treat at least one IL-23p19 related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-IL-23p19 antibody, according to the present invention.

The present invention further provides at least one anti-IL-23p19 antibody method or composition, for diagnosing at least one IL-23 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-IL-23p19 antibody, according to the present invention.

Also provided is a medical device, comprising at least one isolated mammalian anti-IL-23p19 antibody of the invention, wherein the device is suitable for contacting or administering the at least one anti-IL-23p19 antibody, IL-23p19 anti-idiotypic antibody, nucleic acid molecule, compound, protein, and/or composition.

Also provided is an article of manufacture for human pharmaceutical or diagnostic use, comprising packaging material and a container comprising a solution or a lyophilized form of at least one isolated anti-IL-23p19 antibody of the present invention. The article of manufacture can optionally have the container as a component of a delivery device or system.

The present invention further provides any invention described herein.

DESCRIPTION OF THE INVENTION

Figure 1:
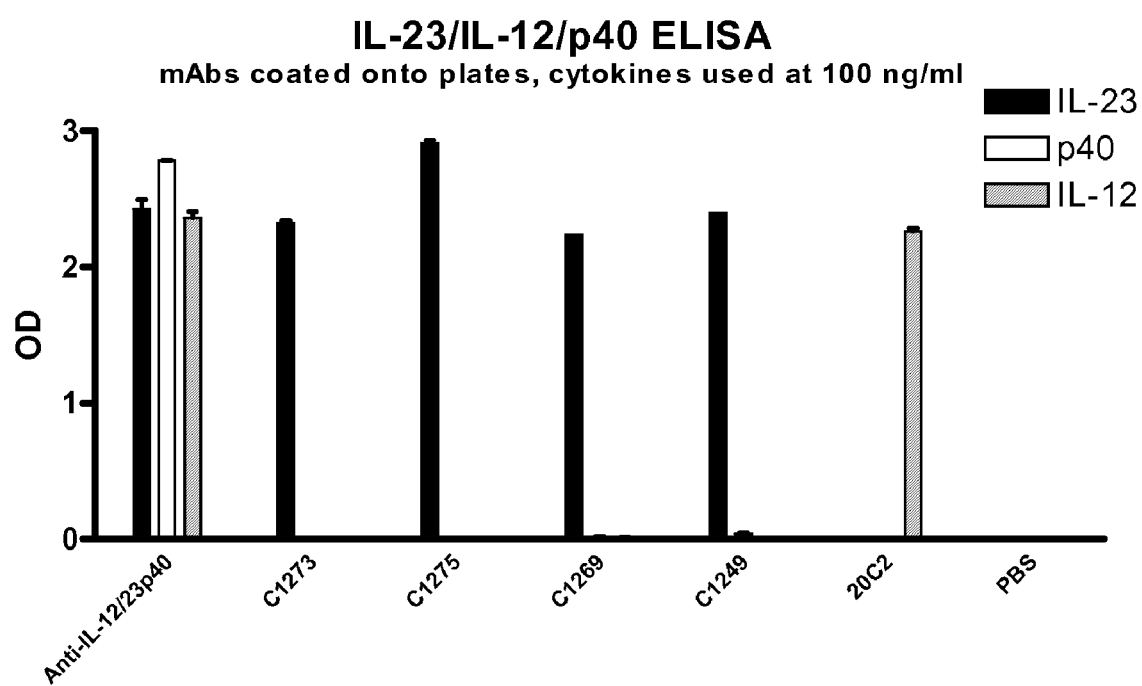
FIG. 1 shows that IL23p19 antibodies bind specifically to hrIL-23 and not hrIL-12 or hrp40 monomer. An anti-IL12/IL23 p40 antibody is shown to bind IL-23, IL-12 and the p40 monomer. An anti-IL12 antibody (20C2) is shown to bind IL-12 only.

The present invention provides isolated, recombinant and/or synthetic anti-IL-23p19 antibodies, including, without limitation, mammalian (e.g., human antibodies) and IL-23p19 anti-idiotype antibodies thereto, as well as compositions and encoding nucleic acid molecules comprising at least one polynucleotide encoding at least one anti-IL-23p19 antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-IL-23p19 antibody," "IL-23p19 antibody," "anti-IL-23p19 antibody portion," or "anti-IL-23p19 antibody fragment" and/or "anti-IL-23p19 antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23p19 antibody, specified portion or variant of the present invention can bind at least one IL-23 molecule, or specified portions, variants or domains thereof.

A suitable anti-IL-23p19 antibody, specified portion, or variant can also optionally affect at least one of IL-23p19 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including, without limitation, antibody mimetics or comprising portions of antibodies that mimic the structure and/or function of an antibody or specified fragment or portion thereof, including, without limitation, single chain antibodies, single domain antibodies, and fragments thereof. Functional fragments include antigen-binding fragments that bind to a human IL-23p19. For example, antibody fragments capable of binding to IL-23p19 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

The term "human antibody," as used herein, is intended to include antibodies having variable and constant regions derived from or closely matching human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Thus, as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to a human germline antibody. Human antibodies have been classified into groupings based on their amino acid sequence similarities, see e.g. http://people.cryst.bbk.ac.uk/~ubcg07s/. Thus, using a sequence similarity search, an antibody with similar linear sequence can be chosen as a template to create "humanized antibodies."

"Humanization" (also called Reshaping or CDR-grafting) is now a well-established technique for reducing the immunogenicity of monoclonal antibodies (mabs) from xenogeneic sources (commonly rodent) and for improving the effector functions (ADCC, complement activation, C1q binding). The engineered mAb is engineered using the techniques of molecular biology, however simple CDR-grafting of the rodent complementarity-determining regions (CDRs) into human frameworks often results in loss of binding affinity and/or specificity of the original mAb. In order to humanize an antibody, the design of the humanized antibody includes variations such as conservative amino acid substitutions in residues of the CDRS, and back substitution of residues from the rodent mAb into the human framework regions (backmutations). The positions can be discerned or identified by sequence comparison for structural analysis or by analysis of a homology model of the variable regions' 3D structure. The process of affinity maturation has most recently used phage libraries to vary the amino acids at chosen positions.

Similarly, many approaches have been used to choose the most appropriate human frameworks in which to graft the rodent CDRs. As the datasets of known parameters for antibody structures increases, so does the sophistication and refinement of these techniques. Consensus or germline sequences from a single antibody or fragments of the framework sequences within each light or heavy chain variable region from several different human mAbs can be used. Another approach to humanization is to modify only surface residues of the rodent sequence with the most common residues found in human mAbs and has been termed "resurfacing" or "veneering." Known human Ig sequences are disclosed, e.g., www.ncbi.nlm.nih.gov/entrez/query.fcgi; www.ncbi.nih.gov/igblast; www.atcc.org/phage/hdb.html; www.kabatdatabase.com/top.html; www.antibodyresource-.com/onlinecomp.html; www.appliedbiosystems.com; www.biodesign.com; antibody.bath.ac.uk; www.unizh.ch; www.cryst.bbk.ac.uk/~ubcg07s; Kabat et al., Sequences of Proteins of Immunological Interest, U.S. Dept. Health (1983), each entirely incorporated herein by reference. Often, the human or humanized antibody is substantially non-immunogenic in humans.

Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes.

Further, when a human antibody is a single chain or single domain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23p19 protein subunit, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule is usually done by affinity chromatography steps. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23p19 antibodies useful in the methods and compositions of the present invention can optionally be characterized by high affinity binding to IL-23p19 and, optionally and preferably, as having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as the incidence of titrable levels of antibodies to the anti-IL-23p19 antibody in patients treated with anti-IL-23p19 antibody as occurring in less than 25% of patients treated, preferably, in less than 10% of patients treated with the recommended dose for the recommended course of therapy during the treatment period.

The isolated nucleic acids of the present invention can be used for production of at least one anti-IL-23p19 antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-23 related condition, selected from, but not limited to, at least one of an immune disorder or disease, a cardiovascular disorder or disease, an infectious, malignant, and/or neurologic disorder or disease, or other known or specified IL-23 related condition.

Such a method can comprise administering an effective amount of a composition or a pharmaceutical composition comprising at least one anti-IL-23p19 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effec- Antibodies of the Present Invention—Production and Generation At least one anti-IL-23p19 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Antibodies that are specific for human IL-23p19 proteins or fragments thereof can be raised against an appropriate immunogenic antigen, such as an isolated IL-23p19 protein and/or a portion thereof (including synthetic molecules, such as synthetic peptides). Other specific or general antibodies, including, without limitation, mammalian antibodies, can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Methods for engineering or humanizing non-human or human antibodies can also be used and are well known in the art. A humanized or engineered antibody may have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/linksl.html; www.recab.uni-hd.de/immuno.bme.nwu.edu; www.mrccpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or engineered or human antibodies engineered with retention of high affinity for the antigen and other favorable biological properties. To achieve this goal, humanized (or human) antibodies can be optionally prepared by a process of analysis of the parental sequences and various conceptual humanized and engineered products using three-dimensional models of the parental, engineered, and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen.

In this way, framework (FR) residues can be selected and combined from the consensus and import sequences so that the desired antibody characteristic, such as increased affinity for the target antigen(s), is achieved.

In addition, the IL-23p19 antibody of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In other embodiments, the IL-23 antibody of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

As disclosed above, one can design an Fc region of the IL-23p19 antibody of the present invention with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the IL-23p19 antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the IL-23p19 antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an IL-23p19 antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the IL-23p19 antibody of the present invention is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. An anti-IL-23p19 antibody can be optionally generated by immunization of a transgenic animal (e.g., mouse, rat, hamster, non-human primate, and the like) capable of producing a repertoire of human antibodies, as described herein and/or as known in the art. Cells that produce an anti-IL-23p19 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770, 428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; 5,223,409, 5,403,484, 5,571, 698, 5,837,500, assigned to Dyax, 5,427,908, 5,580,717, assigned to Affymax; 5,885,793, assigned to Cambridge Antibody Technologies; 5,750,373, assigned to Genentech, 5,618,920, 5,595,898, 5,576,195, 5,698,435, 5,693,493, 5,698,417, assigned to Xoma, Colligan, supra; Ausubel, supra; or Sambrook, supra.

Antibodies of the present invention can also be prepared using at least one anti-IL-23p19 antibody encoding nucleic acid to provide transgenic animals or mammals, such as goats, cows, horses, sheep, rabbits and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-IL-23p19 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein.

The antibodies of the invention can bind human IL-23p19 with a wide range of affinities ($K_D$). In a preferred embodiment, at least one mab of the present invention can optionally bind human IL-23p19 with high affinity. For example, a human or other mAb can bind human IL-23p19 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$, $10^{-14}$, $10^{15}$ or any range or value therein, as determined by surface plasmon resonance or the Kinexa method, as practiced by those of skill in the art.

In one embodiment, the antibodies of the invention bind human IL-23, or more specifically, IL-23p19, with a $K_D$ between about $3.38 \times 10^{-10}$ M and about $4.3 \times 10^{-11}$ M.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.

H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_{on}$, $K_{off}$) are preferably made with standardized solutions of antibody and antigen, and a standardized buffer, such as the buffer described herein.

Certain embodiments of the anti-IL-23p19 antibodies of the invention have the sequences shown in the Sequence Tables below. For example, an anti-IL-23p19 antibody of the invention has one of the light chain CDR1 sequences of SEQ ID NOS:9, 19, 29, and 39; one of the light chain CDR2 sequences of SEQ ID NOS:10, 20, 30, and 40; one of the light chain CDR3 sequences of SEQ ID NOS:11, 21, 31, and 41; one of the heavy chain CDR1 sequences SEQ ID NOS:4, 14, 24, and 34; one of the heavy chain CDR2 sequences SEQ ID NOS:5, 15, 25, and 35; and/or one of the heavy chain CDR1 sequences SEQ ID NOS:6, 16, 26, and 36.

Nucleic Acid Molecules

Using the information provided herein, for example, the nucleotide sequences encoding at least 70-100% of the contiguous amino acids of at least one of the light chain variable regions of SEQ ID NOS:7, 17, 27, and 37 and at least one of the heavy chain variable regions of SEQ ID NOS:2, 12, 22, and 32, specified fragments, variants or consensus sequences thereof, or a deposited vector comprising at least one of these sequences, a nucleic acid molecule of the present invention encoding at least one anti-IL-23p19 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally, with one or more introns, e.g., but not limited to, at least one specified portion of at least one CDR, such as CDR1, CDR2 and/or CDR3 of at least light chain (9, 10, 11, 19, 20, 21, 29, 30, 31, 39, 40, 41) or at least one heavy chain (SEQ ID NOS:4, 5, 6, 14, 15, 16, 24, 25, 26, 34, 35, and 36); nucleic acid molecules comprising the coding sequence for an anti-IL-23p19 antibody or variable region (e.g., light chain variable regions of SEQ ID NOS:7, 17, 27, and 37 and heavy chain variable regions of SEQ ID NOS:2, 12, 22, and 32); and nucleic acid molecules which comprise a nucleotide sequence substantially different from those described above but which, due to the degeneracy of the genetic code, still encode at least one anti-IL-23p19 antibody as described herein and/or as known in the art. Of course, the genetic code is well known in the art. Thus, it would be routine for one skilled in the art to generate such degenerate nucleic acid variants that code for specific anti-IL-23p19 antibodies of the present invention. See, e.g., Ausubel, et al., supra, and such nucleic acid variants are included in the present invention.

As indicated herein, nucleic acid molecules of the present invention which comprise a nucleic acid encoding an anti-IL-23p19 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example, a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells

The present invention also relates to vectors that include isolated nucleic acid molecules of the present invention, host cells that are genetically engineered with the recombinant vectors, and the production of at least one anti-IL-23p19 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23p19 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23p19 Antibodies

An anti-IL-23p19 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one CH1, hinge1, hinge2, hinge3, hinge4, CH2, or CH3 or fragment thereof, further optionally comprising at least one substitution, insertion or deletion), or any portion thereof, that can be incorporated into an antibody of the present invention. An antibody of the invention can include or be derived from any mammal, such as but not limited to, a human, a mouse, a rabbit, a rat, a rodent, a primate, or any combination thereof, and the like.

The isolated antibodies of the present invention comprise the antibody amino acid sequences disclosed herein encoded by any suitable polynucleotide, or any isolated or prepared antibody. Preferably, the human antibody or antigen-binding fragment binds human IL-23p19 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to one or more of the IL-23 receptors or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay.

The capacity of an anti-IL-23p19 antibody to inhibit an IL-23-dependent activity is preferably assessed by at least one suitable IL-23 protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, or γ4).

Antibodies of this type can be prepared by employing a transgenic mouse or other transgenic non-human mammal comprising at least one human light chain (e.g., IgG, IgA, and IgM) transgenes as described herein and/or as known in the art. In another embodiment, the anti-human IL-23p19 antibody comprises an IgG1 heavy chain and an IgG1 light chain.

At least one antibody of the invention binds at least one specified epitope specific to at least one IL-23p19 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. The at least one specified epitope can comprise any combination of at least one amino acid sequence of at least 1-3 amino acids to the entire specified portion of contiguous amino acids of amino acid residues 93-104 and 127-137 of SEQ ID NO:1 (that contains the initial 19 amino acid signal sequence for the p19 protein subunit) (or amino acid residues 74-85 and 108-118 of the p19 sequence without inclusion of the signal sequence), for example, amino acid residues 93, 93-94, 93-95, 93-96, 97-99, 100-102, 127, 127-128, 128-129, etc. of SEQ ID NO:1, etc. that include any portions or combinations of these sequences.

Generally, the antibody or antigen-binding fragment of the present invention will comprise an antigen-binding region that comprises at least one complementarity determining region (CDR1, CDR2 and CDR3) or variant of at least one heavy chain variable region and at least one complementarity determining region (CDR1, CDR2 and CDR3) or variant of at least one light chain variable region. Optionally, the CDR sequences may be derived from human germline sequences or closely match the germline sequences. For example, the CDRs from a synthetic library derived from the original mouse CDRs can be used. These CDRs may be formed by incorporation of conservative substitutions from the original mouse sequence. As a non-limiting example, the antibody or antigen-binding portion or variant can comprise at least one of the heavy chain CDR3, e.g., selected from SEQ ID NOS:6, 16, 26, and 36, and/or a light chain CDR3, e.g., selected from SEQ ID NOS:11, 21, 31, and 41. In a particular embodiment, the antibody or antigen-binding fragment can have an antigen-binding region that comprises at least a portion of at least one heavy chain CDR (i.e., CDR1, CDR2 and/or CDR3) (e.g., those disclosed herein). In another particular embodiment, the antibody or antigen-binding portion or variant can have an antigen-binding region that comprises at least a portion of at least one light chain CDR (i.e., CDR1, CDR2 and/or CDR3) (e.g., those disclosed herein).

In a preferred embodiment, the three heavy chain CDRs and the three light chain CDRs of the antibody or antigen-binding fragment can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23p19 antibody can comprise at least one of a heavy or light chain variable region having a defined amino acid sequence. For example, in a preferred embodiment, the anti-IL-23p19 antibody comprises at least one of at least one heavy chain variable region optionally selected from SEQ ID NOS:3, 13, 23, and 33 and/or at least one light chain variable region optionally selected from SEQ ID NOS:8, 18, 28, and 38. Antibodies that bind to human IL-23p19 and that comprise a defined heavy or light chain variable region can be prepared using suitable methods, such as phage display (Katsube, Y., et al., *Int j Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 or a fragment thereof to elicit the production of antibodies.

If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

Amino Acid Codes

The amino acids that make up anti-IL-23p19 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994) An anti-IL-23p19 antibody of the present invention can include one or more amino acid substitutions, deletions or additions, either from natural mutations or human manipulation, as specified herein. Amino acids in an anti-IL-23p19 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-23p19 antibodies of the present invention can include, but are not limited to, at least one portion, sequence or combination selected from 5 to all of the contiguous amino acids of the variable region sequences of SEQ ID NOS:8, 18, 28, and 38 and SEQ ID NOS:3, 13, 23, and 33.

Non-limiting variants that can enhance or maintain at least one of the listed activities include, but are not limited to, any of the above polypeptides, further comprising at least one mutation corresponding to at least one substitution in the residues varied among the disclosed variant amino acid sequences.

An anti-IL-23p19 antibody can further optionally comprise a polypeptide with an amino acid sequence that varies from the sequence of SEQ ID NOS: 3-6, 8-11, 13-16, 18-21, 23-26, 28-31, 33-36, and 38-41 (e.g., one or more conservative substitutions from the sequences provided herein). Also, the present invention comprises variants of the amino acid sequence of a light chain variable region of SEQ ID NOS:8, 18, 28, and 38 or the amino acid sequence of a heavy chain variable region of SEQ ID NOS:3, 13, 23, and 33.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-1000% or more of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group.

In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{22}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—.

Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

Anti-Idiotype Antibodies to Anti-IL-23p19 Antibody Compositions

In addition to monoclonal anti-IL-23p19 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g., mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

The present invention also provides at least one anti-IL-23p19 antibody composition comprising at least one, at least two, at least three, at least four, at least five, at least six or more anti-IL-23p19 antibodies thereof, as described herein and/or as known in the art that are provided in a non-naturally occurring composition, mixture or form. Such compositions comprising at least one or two full length, C- and/or N-terminally deleted variants, domains, fragments, or specified variants, of the anti-IL-23p19 antibody amino acid sequence selected from the group consisting of: 70-100% of the contiguous amino acids of SEQ ID NOS:3-6, 8-11, 13-16, 18-21, 23-26, 28-31, 33-36, and 38-41, or specified fragments, domains or variants thereof. Preferred anti-IL-23p19 antibody compositions include at least one or two full length, fragments, domains or variants of at least one CDR or LBP containing portions of the anti-IL-23p19 antibody sequence described herein, for example, 70-100% of SEQ ID NOS: 3-6, 8-11, 13-16, 18-21, 23-26, 28-31, 33-36, and 38-41, or specified fragments, domains or variants thereof. Further preferred compositions comprise, for example, 40-99% of at least one of 70-100% of SEQ ID NOS: 3-6, 8-11, 13-16, 18-21, 23-26, 28-31, 33-36, and 38-41, or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from nonnarcotic analgesics or at least one selected from antipyretics, nonsteroidal anti-inflammatory drugs, narcotic or at least one opiod analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, optics, and nasal drugs. The topical drug can be at least one selected from local anti-infectives, scabicides or at least one pediculicide or topical corticosteroid. The nutritional drug can be at least one selected from vitamins, minerals, or calories. See, e.g., contents of *Nursing* 2001 *Drug Handbook, supra.*

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium. The at least one cephalosporin can be at least one selected from cefaclor, cefadroxil, cefazolin sodium, cefdinir, cefepime hydrochloride, cefixime, cefinetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride.

The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of *Nursing* 2001 *Drug Handbook.*)

The at least one inotropic can be at least one selected from aminone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrchloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of *Nursing* 2001 *Drug Handbook*.)

The at least one nonnarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenyloin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of *Nursing* 2001 *Drug Handbook*.)

The at least one cholinergic (e.g., parasymathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of *Nursing* 2001 *Drug Handbook*.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, dornase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of Nursing 2001 Drug Handbook.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates.

The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of Nursing 2001 Drug Handbook.)

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide $^{131}$I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, *bacillus* Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of *Nursing* 2001 *Drug Handbook*.)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatisis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), amd *Micrurus fulvius* antivenin. The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), Rh$_0$(D) immune globulin (human), Rh$_0$(D) immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of *Nursing* 2001 *Drug Handbook*.)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of *Nursing* 2001 *Drug Handbook*.)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook*.)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of *Nursing 2001 Drug Handbook*.)

Anti-IL-23p19 antibody compositions of the present invention can further comprise at least one of any suitable and effective amount of a composition or pharmaceutical composition comprising at least one anti-IL-23p19 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid antiinflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an anti-emetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-28 (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual*, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-IL-23p19 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the anti-IL-23p19 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23p19 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23p19 antibody compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23p19 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23p19 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used as known in the art, such as about 0.0015%, or any range, value, or fraction therein. Non-limiting examples include, no preservative, about 0.1-2% m-cresol (e.g., 0.2, 0.3. 0.4, 0.5, 0.9, 1.0%), about 0.1-3% benzyl alcohol (e.g., 0.5, 0.9, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-IL-23p19 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-IL-23p19 antibody, and a second vial comprising an aqueous diluent of prescribed buffer or preservative, wherein said packaging material comprises a label that instructs a patient to reconstitute the at least one anti-IL-23p19 antibody in the aqueous diluent to form a solution that can be held over a period of twenty-four hours or greater.

The at least one anti-IL-23p19 antibody used in accordance with the present invention can be produced by recombinant means, including from mammalian cell or transgenic preparations, or can be purified from other biological sources, as described herein or as known in the art.

The range of at least one anti-IL-23p19 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-IL-23p19 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23p19 antibody and preservative in an aqueous diluent is carried out using conventional dissolution and mixing procedures. To prepare a suitable formulation, for example, a measured amount of at least one anti-IL-23p19 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-IL-23p19 antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biological activity of the protein for extended periods of time, thus allowing a package label indicating that the solution can be held and/or used over a period of 6, 12, 18, 24, 36, 48, 72, or 96 hours or greater.

If preserved diluent is used, such label can include use up to 1-12 months, one-half, one and a half, and/or two years.

The solutions of at least one anti-IL-23p19 antibody of the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23p19 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23p19 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors and needle free IV infusion sets.

The products presently claimed include packaging material. The packaging material provides, in addition to the information required by the regulatory agencies, the conditions under which the product can be used. The packaging material of the present invention provides instructions to the patient to reconstitute the at least one anti-IL-23p19 antibody in the aqueous diluent to form a solution and to use the solution over a period of 2-24 hours or greater for the two vial, wet/dry, product. For the single vial, solution product, the label indicates that such solution can be used over a period of 2-24 hours or greater.

The presently claimed products are useful for human pharmaceutical product use.

The formulations of the present invention can be prepared by a process that comprises mixing at least one anti-IL-23p19 antibody and a selected buffer, preferably, a phosphate buffer containing saline or a chosen salt. Mixing the at least one anti-IL-23p19 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-IL-23p19 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23p19 antibody may result in other than a clear solution of lyophilized powder comprising the antibody. Among non-clear solutions are formulations comprising particulate suspensions, said particulates being a composition containing the anti-IL-23p19 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid.

Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968.

The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one anti-IL-23p19 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one IL-23 related disease, in a cell, tissue, organ, animal, or patient, as known in the art or as described herein, using at least one IL-23p19 antibody of the present invention, e.g., administering or contacting the cell, tissue, organ, animal, or patient with a therapeutic effective amount of IL-23p19 antibody. The present invention also provides a method for modulating or treating at least one IL-23 related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one IL-23 related immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, osteolysis, aseptic loosening of orthopedic implants, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, acute coronary syndrome, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-IL-23p19 antibody to a cell, tissue, organ, animal or patient in need of such modulation, treatment or therapy.

The present invention also provides a method for modulating or treating at least one IL-23 related infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis*, *mycobacterium avium* intracellulare, *pneumocystis carinii* pneumonia, pelvic inflammatory disease, orchitis/epidydimitis, *legionella*, lyme disease, influenza a, epstein-barr virus, viral-associated hemaphagocytic syndrome, viral encephalitis/aseptic meningitis, and the like.

The present invention also provides a method for modulating or treating at least one IL-23 related malignant disease in a cell, tissue, organ, animal or patient, including, but not limited to, at least one of: leukemia, acute leukemia, acute lymphoblastic leukemia (ALL), acute lymphocytic leukemia, B-cell, T-cell or FAB ALL, acute myeloid leukemia (AML), acute myelogenous leukemia, chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometiral cancer, head cancer, neck cancer, hereditary non-polyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

The present invention also provides a method for modulating or treating at least one IL-23 related neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; Dementia pugilistica; neurotraumatic injury (e.g., spinal cord injury, brain injury, concussion, repetitive concussion); pain; inflammatory pain; autism; depression; stroke; cognitive disorders; epilepsy; and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, $16^{th}$ Edition, Merck & Company, Rahway, N.J. (1992).

The present invention also provides a method for modulating or treating at least one IL-23 related wound, trauma or tissue injury or related chronic condition, in a cell, tissue, organ, animal or patient, including, but not limited to, at least one of: bodily injury or a trauma associated with oral surgery including periodontal surgery, tooth extraction(s), endodontic treatment, insertion of tooth implants, application and use of tooth prosthesis; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound.

Wounds and/or ulcers are normally found protruding from the skin or on a mucosal surface or as a result of an infarction in an organ ("stroke"). A wound may be a result of a soft tissue defect or a lesion or of an underlying condition. In the present context, the term "skin" relates to the outermost surface of the body of an animal, including a human, and embraces intact or almost intact skin as well as an injured skin surface. The term "mucosa" relates to undamaged or damaged mucosa of an animal, such as a human, and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore," "lesion," "necrosis," and "ulcer." Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

The term "wound" used in the present context denotes any wound (see below for a classification of wounds) and at any particular stage in the healing process, including the stage before any healing has initiated or even before a specific wound like a surgical incision is made (prophylactic treatment). Examples of wounds which can be prevented and/or treated in accordance with the present invention are, e.g., aseptic wounds, contused wounds, incised wounds, lacerated wounds, non-penetrating wounds (i.e., wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores, etc.

Examples of ulcers are, e.g., a peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, and veneral ulcer, e.g., caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore, as mentioned above, in the present context the term "wound" encompasses the terms "ulcer," "lesion," "sore" and "infarction," and the terms are indiscriminately used unless otherwise indicated.

The kinds of wounds to be treated according to the invention include also (i) general wounds, such as, e.g., surgical, traumatic, infectious, ischemic, thermal, chemical and bullous wounds;

(ii) wounds specific for the oral cavity, such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and (iii) wounds on the skin, such as, e.g., neoplasm, burns (e.g. chemical, thermal), lesions (bacterial, viral, autoimmunological), bites and surgical incisions. Another way of classifying wounds is as (i) small tissue loss due to surgical incisions, minor abrasions and minor bites, or as (ii) significant tissue loss. The latter group includes ischemic ulcers, pressure sores, fistulae, lacerations, severe bites, thermal burns and donor site wounds (in soft and hard tissues) and infarctions.

Other wounds that are of importance in connection with the present invention are wounds like ischemic ulcers, pressure sores, fistulae, severe bites, thermal burns and donor site wounds. Ischemic ulcers and pressure sores are wounds which normally only heal very slowly and especially in such cases, an improved and more rapid healing process is of course of great importance for the patient. Furthermore, the costs involved in the treatment of patients suffering from such wounds are markedly reduced when the healing is improved and takes place more rapidly.

Donor site wounds are wounds which, e.g., occur in connection with removal of hard tissue from one part of the body to another part of the body, e.g., in connection with transplantation. The wounds resulting from such operations are very painful and an improved healing is therefore most valuable. The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

The present invention also provides a method for modulating or treating psoriasis, psoriatic arthritis, Crohn's disease, multiple sclerosis, and optic neuritis, among the other diseases listed above as IL-23 related, in a cell, tissue, organ, animal, or patient including, but not limited to, at least one of immune related disease, cardiovascular disease, infectious, malignant and/or neurologic disease. Such a method can optionally comprise administering an effective amount of at least one composition or pharmaceutical composition comprising at least one anti-IL-23p19 antibody to a cell, tissue, organ, animal or patient in need of such modulation, treatment or therapy.

Any method of the present invention can comprise administering an effective amount of a composition or pharmaceutical composition comprising at least one anti-IL-23p19 antibody to a cell, tissue, organ, animal or patient in need of such modulation, treatment or therapy. Such a method can optionally further comprise co-administration or combination therapy for treating such diseases or disorders, wherein the administering of said at least one anti-IL-23p19 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J. each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF antibodies (e.g., at least one TNF antagonist as defined above), antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or, preferably, in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

An example of a TNF antibody or antagonist is the chimeric antibody cA2. Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention.

TNF receptor multimeric molecules useful in the present invention comprise all or a functional portion of the ECD of two or more TNF receptors linked via one or more polypeptide linkers or other nonpeptide linkers, such as polyethylene glycol (PEG). An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116, 964; Capon et al., U.S. Pat. No. 5,225,538; and Capon et al., *Nature* 337:525-531 (1989), which references are entirely incorporated herein by reference.

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments

Any method of the present invention can comprise a method for treating an IL-23 mediated disorder, comprising administering an effective amount of a composition or pharmaceutical composition comprising at least one anti-IL-23p19 antibody to a cell, tissue, organ, animal or patient in need of such modulation, treatment or therapy. Such a method can optionally further comprise co-administration or combination therapy for treating such diseases or disorders, wherein the administering of said at least one anti-IL-23p19 antibody, specified portion or variant thereof, further comprises administering before, concurrently, and/or after, at least one selected from an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like, at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Such drugs are well known in the art, including formulations, indications, dosing and administration for each presented herein (see, e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

Typically, treatment of pathologic conditions is effected by administering an effective amount or dosage of at least one anti-IL-23p19 antibody composition that total, on average, a range from at least about 0.01 to 500 milligrams of at least one anti-IL-23p19 antibody per kilogram of patient per dose, and, preferably, from at least about 0.1 to 100 milligrams antibody/ kilogram of patient per single or multiple administration, depending upon the specific activity of the active agent contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include about 0.1-99 and/or 100-500 mg/kg/administration, or any range, value or fraction thereof, or to achieve a serum concentration of about 0.1-5000 µg/ml serum concentration per single or multiple administration, or any range, value or fraction thereof. A preferred dosage range for the anti-IL-23p19 antibody of the present invention is from about 1 mg/kg, up to about 3, about 6 or about 12 mg/kg of body weight of the patient.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and about 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of at least one anti-IL-23p19 antibody according to the present invention. While pulmonary administration is used in the following description, other modes of administration can be used according to the present invention with suitable results. IL-23p19 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839, 446 entirely incorporated herein by reference.

Alternative Delivery

The invention further relates to the administration of at least one anti-IL-23p19 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means.

At least one anti-IL-23p19 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Pulmonary/Nasal Administration

For pulmonary administration, preferably, at least one anti-IL-23p19 antibody composition is delivered in a particle size effective for reaching the lower airways of the lung or sinuses. According to the invention, at least one anti-IL-23p19 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use formulations suitable for the administration for the dispensing of antibody in an aerosol.

Such aerosols can be comprised of either solutions (both aqueous and non aqueous) or solid particles.

Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458, 135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404, 871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention.

Preferably, a composition comprising at least one anti-IL-23p19 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g., less than about 10 μm, preferably about 1-5 μm, for good respirability.

Administration of IL-23p19 Antibody Compositions as a Spray

A spray including IL-23p19 antibody composition can be produced by forcing a suspension or solution of at least one anti-IL-23p19 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-IL-23p19 antibody composition delivered by a sprayer have a particle size less than about 10 μm, preferably, in the range of about 1 μm to about 5 μm, and, most preferably, about 2 μm to about 3 μm.

Formulations of at least one anti-IL-23p19 antibody composition suitable for use with a sprayer typically include antibody composition in an aqueous solution at a concentration of about 0.1 mg to about 100 mg of at least one anti-IL-23p19 antibody composition per ml of solution or mg/gm, or any range, value, or fraction therein. The formulation can include agents, such as an excipient, a buffer, an isotonicity agent, a preservative, a surfactant, and, preferably, zinc. The formulation can also include an excipient or agent for stabilization of the antibody composition, such as a buffer, a reducing agent, a bulk protein, or a carbohydrate. Bulk proteins useful in formulating antibody compositions include albumin, protamine, or the like. Typical carbohydrates useful in formulating antibody compositions include sucrose, mannitol, lactose, trehalose, glucose, or the like. The antibody composition formulation can also include a surfactant, which can reduce or prevent surface-induced aggregation of the antibody composition caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein, such as IL-23p19 antibodies, or specified portions or variants, can also be included in the formulation.

Administration of IL-23p19 Antibody Compositions by a Nebulizer

Antibody compositions of the invention can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition either directly or through a coupling fluid, creating an aerosol including the antibody composition. Advantageously, particles of antibody composition delivered by a nebulizer have a particle size less than about 10 µm, preferably, in the range of about 1 µm to about 5 µm, and, most preferably, about 2 µm to about 3 µm.

Formulations of at least one anti-IL-23p19 antibody suitable for use with a nebulizer, either jet or ultrasonic, typically include a concentration of about 0.1 mg to about 100 mg of at least one anti-IL-23p19 antibody protein per ml of solution. The formulation can include agents, such as an excipient, a buffer, an isotonicity agent, a preservative, a surfactant, and, preferably, zinc. The formulation can also include an excipient or agent for stabilization of the at least one anti-IL-23p19 antibody composition, such as a buffer, a reducing agent, a bulk protein, or a carbohydrate.

Bulk proteins useful in formulating at least one anti-IL-23p19 antibody compositions include albumin, protamine, or the like. Typical carbohydrates useful in formulating at least one anti-IL-23p19 antibody include sucrose, mannitol, lactose, trehalose, glucose, or the like. The at least one anti-IL-23p19 antibody formulation can also include a surfactant, which can reduce or prevent surface-induced aggregation of the at least one anti-IL-23p19 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein, such as antibody protein, can also be included in the formulation.

Administration of IL-23p19 Antibody Compositions by a Metered Dose Inhaler

In a metered dose inhaler (MDI), a propellant, at least one anti-IL-23p19 antibody, and any excipients or other additives are contained in a canister as a mixture including a liquefied compressed gas. Actuation of the metering valve releases the mixture as an aerosol, preferably containing particles in the size range of less than about 10 µm, preferably, about 1 µm to about 5 µm, and, most preferably, about 2 µm to about 3 µm. The desired aerosol particle size can be obtained by employing a formulation of antibody composition produced by various methods known to those of skill in the art, including jet-milling, spray drying, critical point condensation, or the like. Preferred metered dose inhalers include those manufactured by 3M or Glaxo and employing a hydrofluorocarbon propellant. Formulations of at least one anti-IL-23p19 antibody for use with a metered-dose inhaler device will generally include a finely divided powder containing at least one anti-IL-23p19 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably, the propellant is a hydrofluorocarbon. The surfactant can be chosen to stabilize the at least one anti-IL-23p19 antibody as a suspension in the propellant, to protect the active agent against chemical degradation, and the like. Suitable surfactants include sorbitan trioleate, soya lecithin, oleic acid, or the like. In some cases, solution aerosols are preferred using solvents, such as ethanol. Additional agents known in the art for formulation of a protein can also be included in the formulation. One of ordinary skill in the art will recognize that the methods of the current invention can be achieved by pulmonary administration of at least one anti-IL-23p19 antibody composition via devices not described herein.

Oral Formulations and Administration

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and antibodies and a combination of at least two surfactants intended for oral, buccal, mucosal, nasal, pulmonary, vaginal transmembrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,871,753 and used to deliver biologically active agents orally are known in the art.

Mucosal Formulations and Administration

A formulation for orally administering a bioactive agent encapsulated in one or more biocompatible polymer or copolymer excipients, preferably, a biodegradable polymer or copolymer, affording microcapsules which due to the proper size of the resultant microcapsules results in the agent reaching and being taken up by the folliculi lymphatic aggregati, otherwise known as the "Peyer's patch," or "GALT" of the animal without loss of effectiveness due to the agent having passed through the gastrointestinal tract. Similar folliculi lymphatic aggregati can be found in the bronchei tubes (BALT) and the large intestine. The above-described tissues are referred to in general as mucosally associated lymphoreticular tissues (MALT). For absorption through mucosal surfaces, compositions and methods of administering at least one anti-IL-23p19 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695).

Transdermal Formulations and Administration

For transdermal administration, the at least one anti-IL-23p19 antibody is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599).

Prolonged Administration and Formulations

It can be desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the compounds of the present invention or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLES

Example 1

Subunit Specificity of IL-23p19 Monoclonal Antibodies

Purified mouse anti-human IL-23 mAbs were evaluated in cytokine capture ELISA to determine their antigen subunit specificity. Briefly, IL-23 mAbs were coated onto plates and incubated with 100 ng/ml (hr=human recombinant) hrIL-23, hrIL-12, and hrp40, respectively. Following incubation with biotinylated anti-p40 mAb, the binding was detected using HRP-conjugated streptavidin. An anti-p40 mAb and an anti-IL-12 mAb (20C2, Catalog No. 555065, BD Pharmingen, San Diego, Calif.) with known specificity were used as controls.

FIG. 1 demonstrates that four mAbs bind specifically hrIL-23 and not hrIL-12 or hrp40 monomer. Because the IL-23p19 subunit must covalently associate with p40 to be secreted from mammalian cells, IL-23 mAbs that do not recognize p40 monomer must bind either the IL-23p19 subunit alone or a joint epitope of the p19-p40 heterodimer. Therefore, these IL-23 mAbs are referred to as IL-23p19 mAbs.

Figure 2:
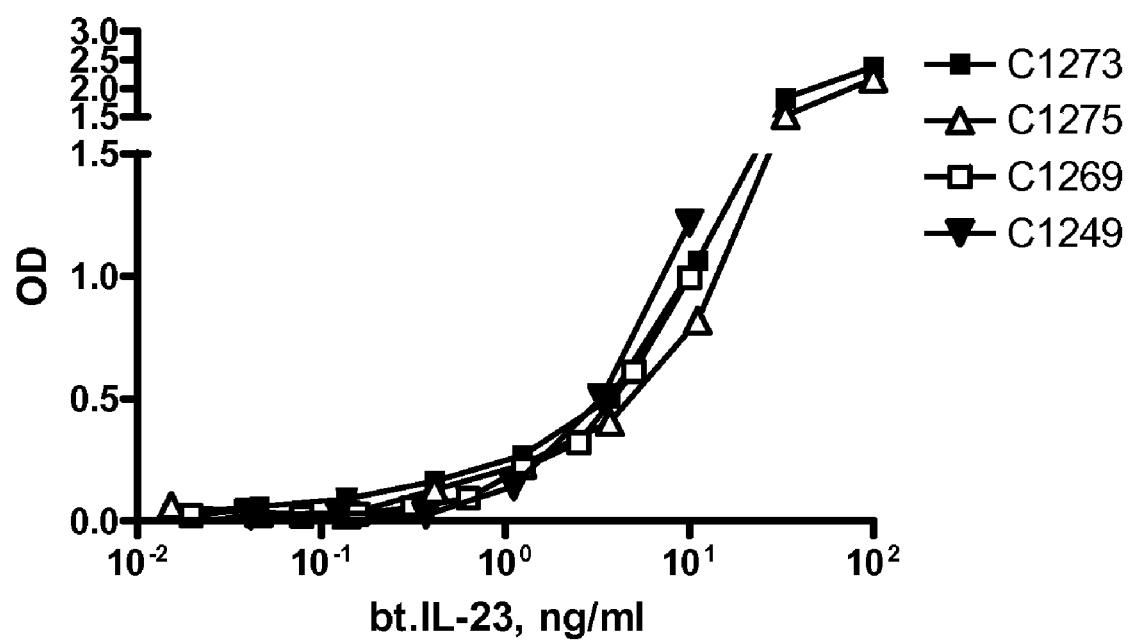
FIG. 2 shows the IL-23 binding to plate-immobilized IL-23p19 antibodies of the invention in which all four antibodies tested show similar binding curves.

All four anti-human IL-23p19 mAbs demonstrate similar binding curves to hrIL-23 (FIG. 2) and subsequent BIAcore analysis demonstrated affinities ranging from 43-338 pM. It was further determined that these IL-23 mAbs do not cross-react with murine IL-23 (data not shown).

Example 2

Inhibition of IL-23 Receptor Binding by IL-23p19 mAbs

Figure 3A:
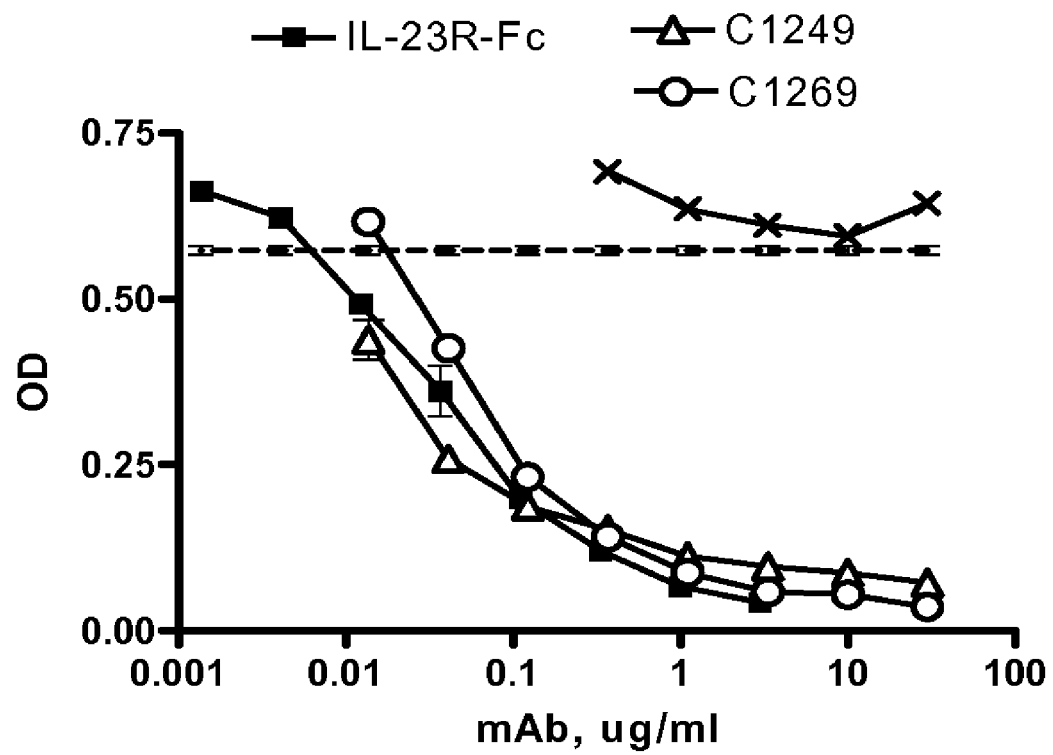
FIG. 3A shows that antibodies C1249 and C1269 block normal IL-23/IL-23R binding.
Figure 3B:
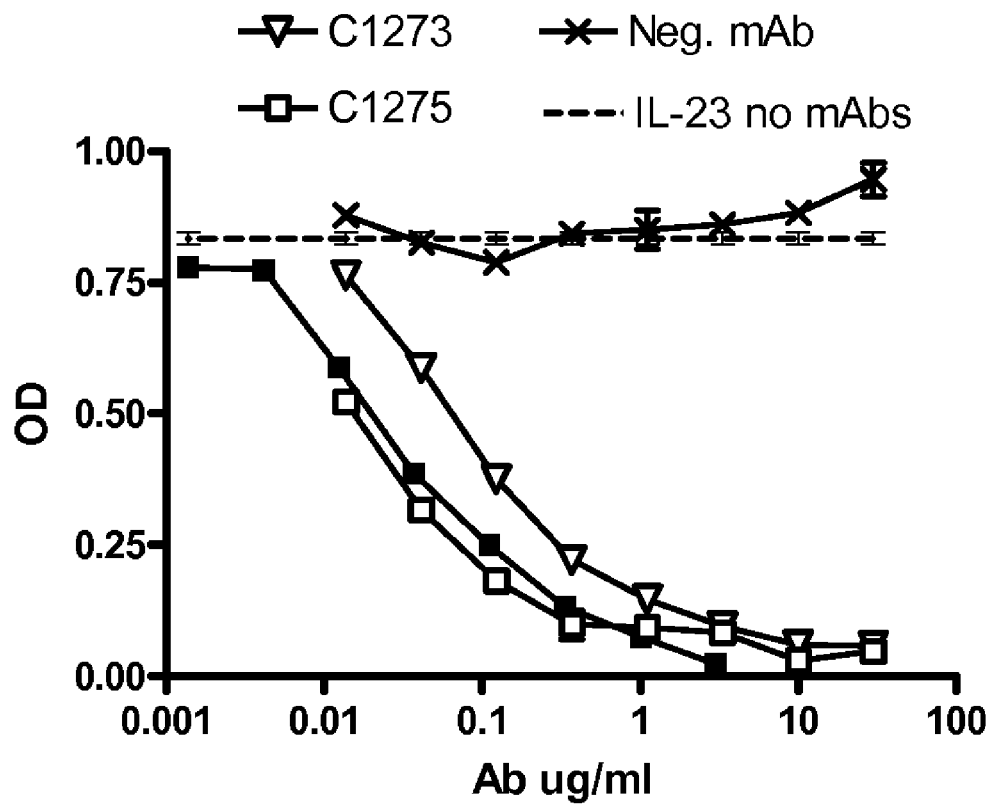
FIG. 3B shows that antibodies C1273 and C1275 block normal IL-23/IL-23R binding.

To demonstrate that the IL-23p19 mAbs are neutralizing antibodies against the p19 subunit, the mAbs were tested for their inhibition of IL-23 and IL-23R binding. In this experiment, IL-23R was immobilized on a plate. Biotinylated hrIL-23 was added to the plate either alone or after preincubation with individual IL-23p19 mAbs. Soluble IL-23R (IL-23R-Fc) was used as a positive control. IL-23 binding was detected with HRP-conjugated streptavidin. As shown in FIG. 3, all four IL-23p19 mAbs were able to prevent IL-23/IL-23R binding with comparable potency to soluble IL-23R-Fc. In contrast, when IL-12Rβ1 was immobilized on a plate, none of the IL-23p19 mAbs were able to inhibit IL-23/IL-12Rβ1 binding (data not shown). Similarly, the IL-23p19 mAbs do not block IL-12/IL-12Rβ1 binding (data not shown). The selective inhibition of IL-23/IL-23R binding and the lack of interference with IL-12 or IL-23 binding to IL-12Rβ1 further demonstrates that these IL-23p19 mAbs do not bind the p40 subunit and thus are neutralizing anti-human IL-23p19 antibodies.

Example 3

Neutralization of IL-23 Biological Function by IL-23p19 mAbs

IL-23 is known to induce intracellular STAT3 phosphorylation and IL-17 production by T cells. Therefore, the IL-23p19 mAbs were tested for their ability to inhibit these biological functions of human IL-23.

In one experiment, natural killer (NKL) cells were stimulated with hrIL-23 either alone or after preincubation with individual IL-23p19 mAbs. Treated cells were stained with fluorochrome-conjugated anti-phospho-STAT3 antibodies and analyzed by intracellular flow cytometry. It was shown that all four IL-23p19 mAbs inhibit STAT3 phosphorylation with comparable potency to a neutralizing anti-p40 mAb.

Figure 4:
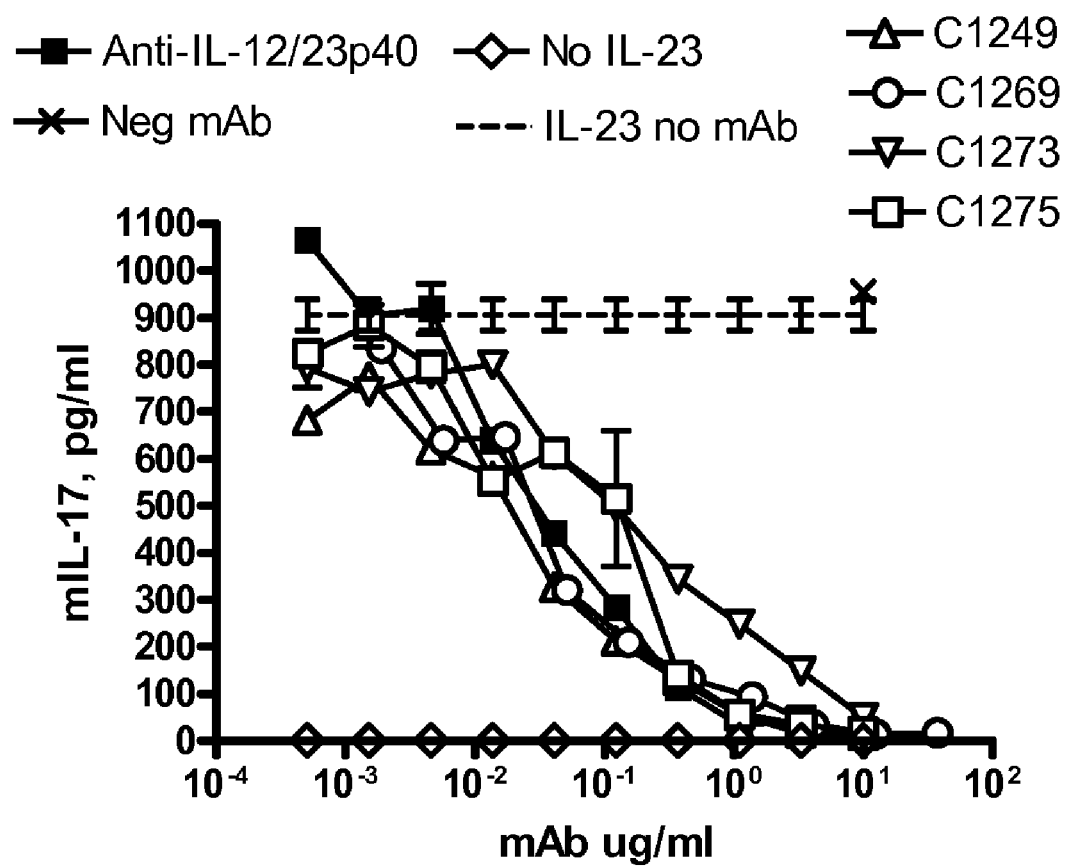
FIG. 4 shows that the IL-23p19 antibodies of the invention inhibit hrIL-23 mediated IL-17 production.
Figure 5:
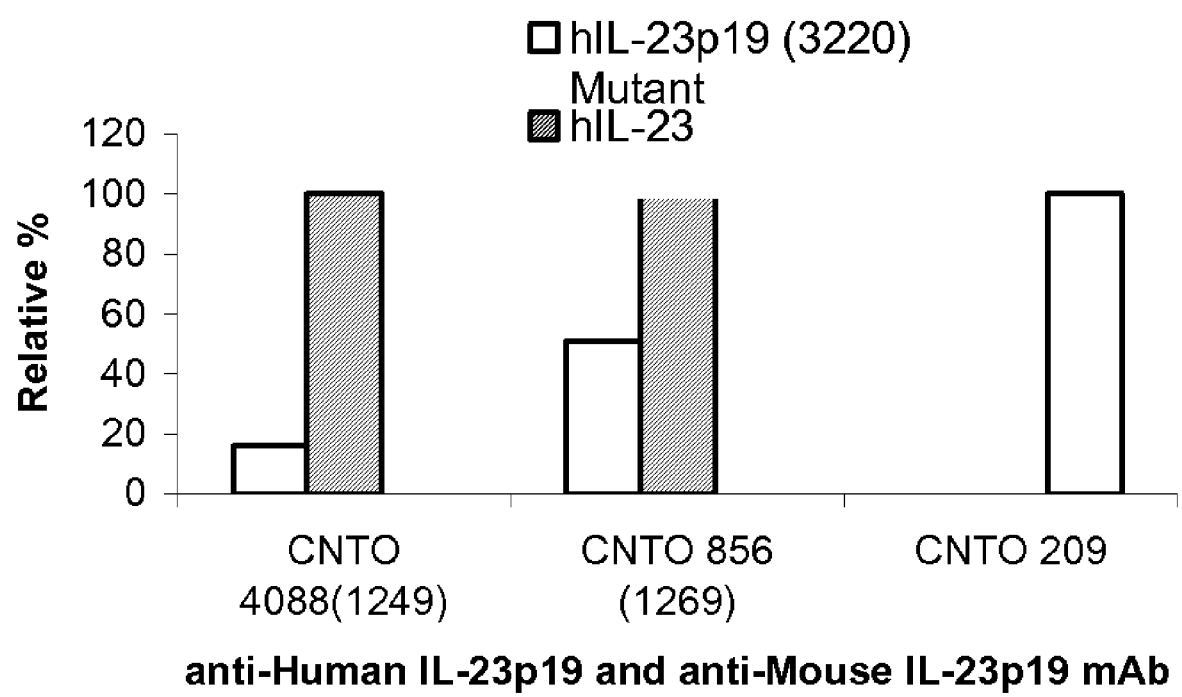
FIG. 5 shows the impact of IL-23 Mutations on Binding of C1249, C1269 and CNTO 209.
Figure 6:
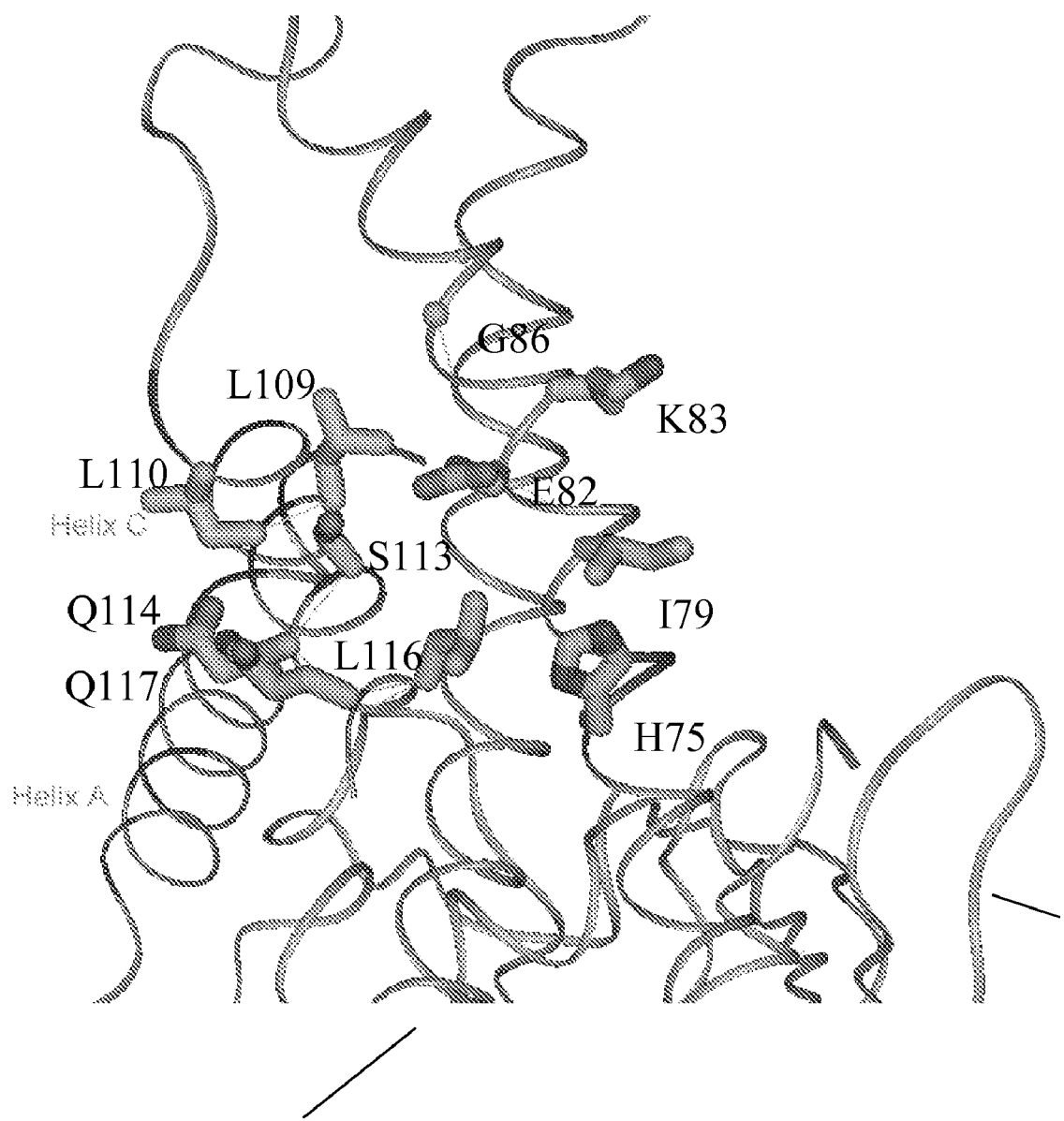
FIG. 6 shows a structural model of human IL-23 in a ribbons representation.

In another experiment, freshly isolated murine splenocytes were treated with hrIL-23 preincubated with titrated IL-23p19 mAbs or control mAbs. hrIL-23 with no antibody preincubation was used as the positive control. After 3 days in culture, cell supernatants were collected and assayed by ELISA using IL-17 ELISA duo set (R&D Systems). As shown in FIG. 4, IL-23p19 mAbs inhibit hrIL-23 mediated IL-17 production. These mAbs were also shown to inhibit native human IL-23 (produced by human PBMC) mediated IL-17 production.

In comparison, IL-23p19 mAbs were also tested for their ability to inhibit IL-12 induced IFNγ production. Briefly, NK92MI cells were treated with IL-12 preincubated with titrated IL-23p19 mAbs or control mAbs. IL-12 with no antibody preincubation was used as the positive control. ELISA analysis performed 24 hours post-stimulation showed no effect of IL-23p19 mAbs on IL-12 induced IFNγ production demonstrating that the antibodies do not bind to the p40 subunit shared by IL-12 and IL-23.

Example 4

Epitope Identification of IL-23p19 mAbs and Competitive Binding

Competition binding analysis was performed to determine if the four neutralizing IL-23p19 mAbs bind to similar or different IL-23p19 epitopes. IL-23 mAbs were individually coated on ELISA plates. Competing mAbs were added, followed by the addition of biotinylated hrIL-23. For positive control, the same mAb for coating was used as the competing mAb ("self-competition"). IL-23 binding was detected using streptavidin. C1269, C1273 and C1275 all show cross-competition indicating binding to a spacially similar site. C1249 shows little or no competition with C1269 or C1273 and partial inhibition of C1275. These results indicate that the mAbs recognize similar or partially overlapping epitopes on IL-23.

Figure 7:
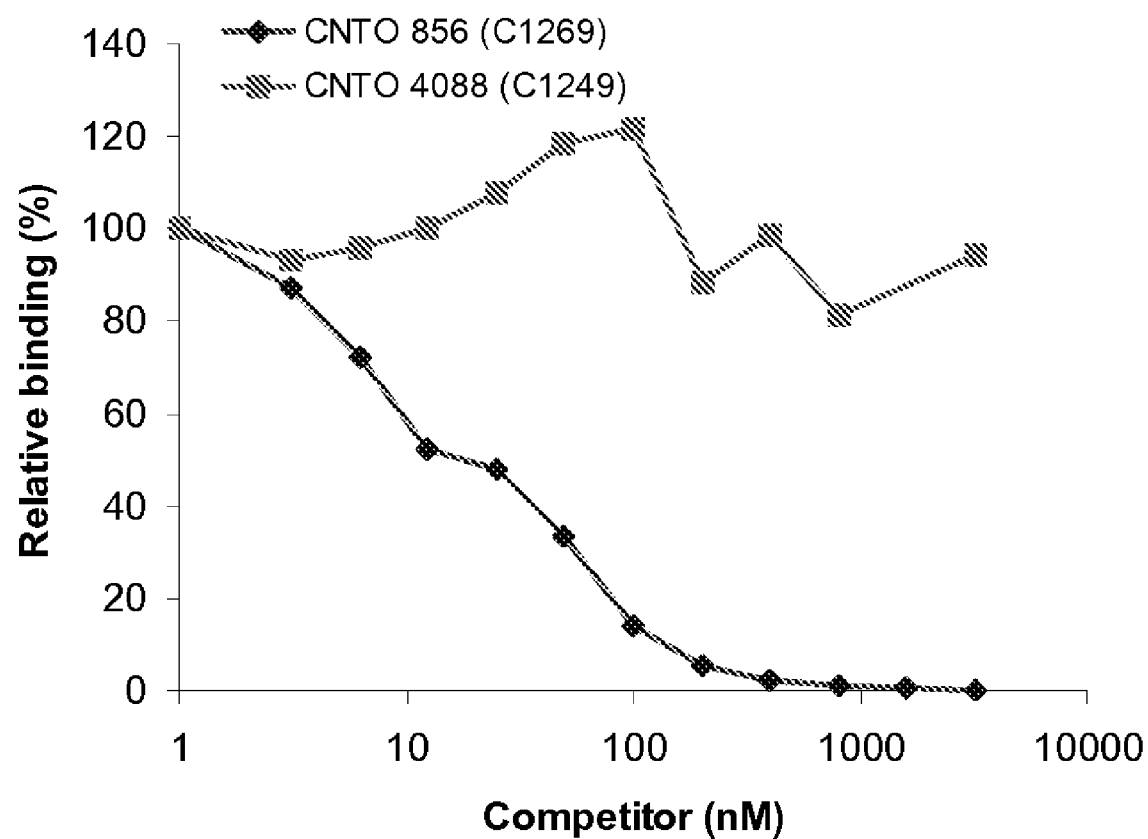
FIG. 7 shows the results of competition analysis of antibodies C1249 and C1269.
Figure 8A:
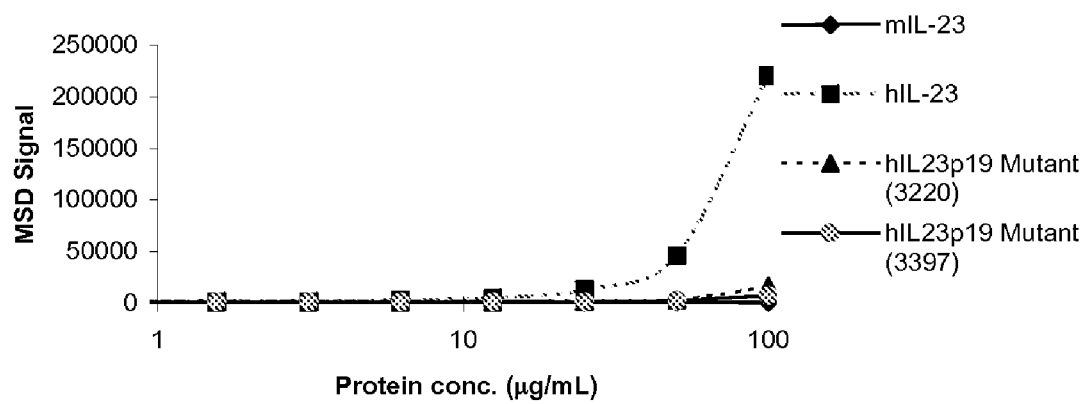
FIG. 8A shows an ELISA analysis of IL-23 mutant proteins binding to antibody C1249.
Figure 8B:
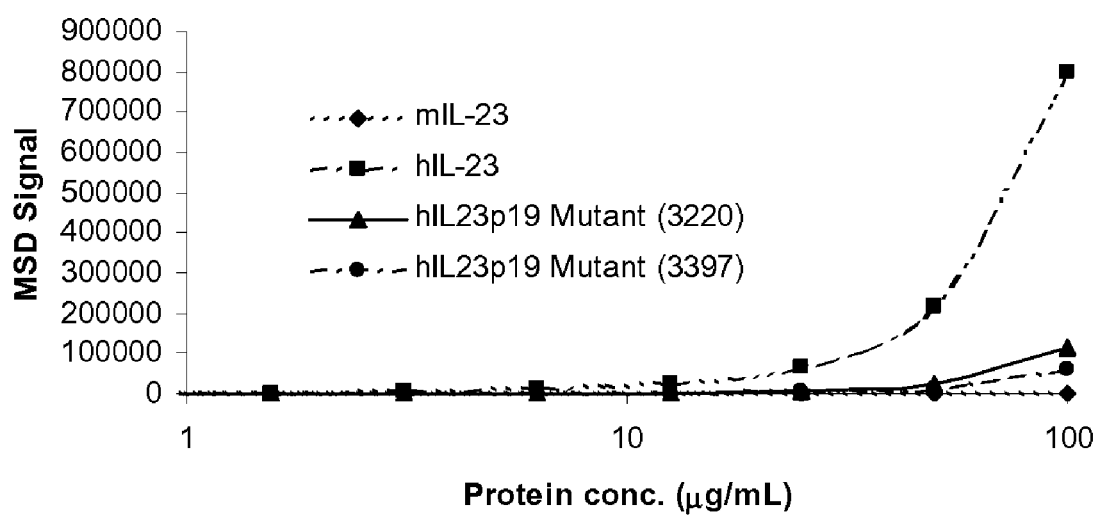
FIG. 8B shows an ELISA analysis of IL-23 mutant proteins binding to antibody C1269.
Figure 9:
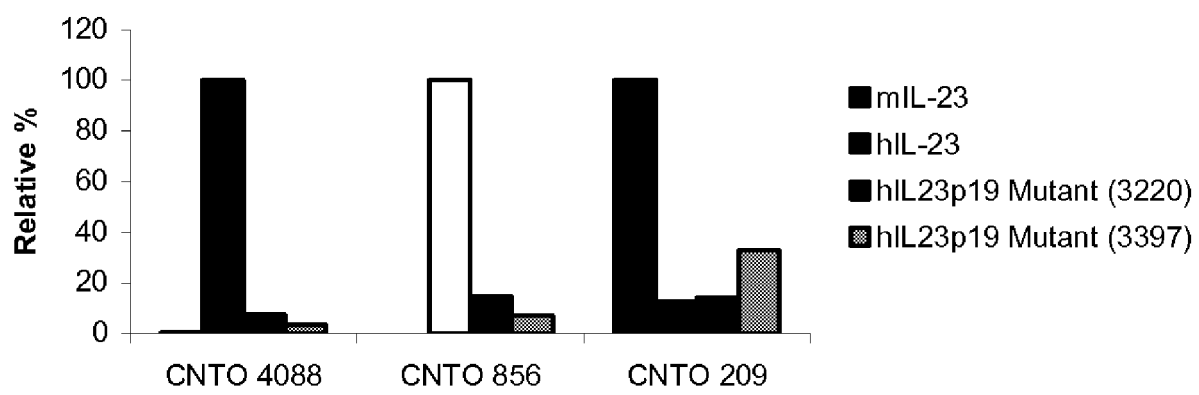
FIG. 9 shows a comparison of the relative binding activity for IL-23 mutant proteins binding to C1249, C1269 and control antibody.

Competition ELISA of labeled C1269 antibody bound to IL-23 was performed as shown in FIG. 7. 5 μL of a 20 μg/ml hIL-23 coated on plate, mixed with 10 nM of labeled C1269 and serially diluted from 3000 nM to 0 unlabeled competitors, C1269 and C1249, in 25 μL. Relative binding was calculated by setting the signal in the absence of competitor to 100%. The results indicate that antibodies C1249 and C1269 do not compete for the same binding epitope.

To directly map their binding epitopes, the IL-23p19 mAbs, 75 μg of C1249 or mouse IgG, was mixed with about 65 μg of IL-23 and incubated at 4° C. overnight. The antigen-antibody complex was isolated by gel chromatography and transferred into digestion buffer (0.1M Tris-HCL pH 8.5) using a 100,000 NMWL filter unit. Then, 4 μg of trypsin (0.16 units) in digestion buffer was added and incubated for 2 hours at 37° C. After incubation, the complexes were captured by Protein G beads, washed twice with PBS and once with ammonium bicarbonate, and the captured peptides eluted in 30 μL of elution buffer (10% Acetonitrile, 0.5% TFA). Complex formation and trypsin digestion of C1269 was carried out in the same manner.

The eluted peptides were analyzed by MALDI-TOF mass spectrometry as described below. Eluents of the trypsin-digest complex were desalted by pipetting the sample through a C18 Zip Tip, the zip tip was wetted with 100% Acetonitrile followed by equilibration with 0.1% TFA. The eluent was then bound to the media, washed with 0.1% TFA and eluted in a volume of 2 μL α-cyano matrix (10 mg/mL α-cyano, 0.1% TFA, 50% Acetonitrile in water) and directly spotted on the MALDI-TOF target. The MALDI-TOF (Voyager-DE™ STR, ABI) was calibrated with Calibration mixture 2 (ABI). Spectra were obtained at laser intensity between 1500-1800 units and acquisition mass range from 800 to 5000 m/z.

One p19 peptide at m/z=1248 ($_{74}$IHQGLIFYEK$_{83}$) was captured by both the C1249 and C1269 mAbs. However, with C1269, this peptide was less intense and may be non-specifically bound. These results indicate that the region $_{74}$IHQGLIFYEK$_{83}$ contributes to the binding epitope for C1249 and C1269.

Epitope-Analysis by Swap Mutagenesis of huIL-23p19/muIL-23p19 Proteins

It has been observed that C1269 and C1249 do not bind to mouse IL-23, however, C1269, but not C1249, neutralizes native IL-23 from cynomolgus monkey. Therefore, sequence differences among human, cynomolgus monkey, and mouse IL-23p19 were analyzed to identify putative binding regions for these monoclonal antibodies. The p19 subunit of cynomolgus monkey was cloned and sequenced at Centocor. Alignment of the p19 sequences from human, cynomolgus and mouse is shown from the region identified as comprising at least a portion of the epitope region for the antibodies of the present invention—$_{74}$IHQGLIFYEK$_{83}$. In this 10-residue amino acid region, there is only a single difference at H75 between human and cynomolgus monkey IL-23p19. This indicates that H75 is critical for the binding of C1249, which does not neutralize cynomolgus IL-23p19, but does not appear to be critical for binding of C1269.

Based on the sequence alignment, species swap mutagenesis was performed. A mutant human IL-23 protein (designated "3220") was generated in which the tryptic peptide region was mutated to the mouse sequence, $_{74}$IRQGLAFYKH$_{83}$, with the four mutations highlighted in bold (four single point mutations in 3220-Human $_{75}$His→Mouse $_{75}$Arg, Human $_{79}$Ile→Mouse $_{79}$Ala, Human $_{82}$Glu→Mouse $_{82}$Lys and Human $_{83}$Lys→Mouse $_{83}$His). A second mutant protein (designated "3397") was constructed that incorporates the D and K substitutions immediately C-terminal of this peptide-$_{74}$IRQGLAFYKHLLDSDIFK$_{91}$ (from wild-type $_{74}$IHQGLIFYEKLLGSDOFT$_{91}$) with the six mutations highlighted in bold (the four mutations of 3220 along with two additional single point mutations—Human $_{75}$His→Mouse $_{75}$Arg, Human $_{79}$Ile→Mouse $_{79}$Ala, Human $_{82}$Glu→Mouse $_{82}$Lys and Human $_{83}$Lys→Mouse $_{83}$His, Human $_{86}$Gly→Mouse $_{86}$Asp and Human $_{91}$Thr→Mouse $_{91}$Lys).

To assess binding specificity for the mutant proteins, ELISA binding was carried out for C1249, C1269, as well as the control surrogate antibody CNTO 209 (rat anti-mouse IL-23p19). The results are shown in FIGS. 8A, 8B, and 9. The ELISA results show that the mutations in IL-23p19 (3220) reduced the binding activity to C1249 and C1269 by more than 80% (FIG. 5 and FIGS. 8A and 8B). The additional substitutions in mutant 3397 further reduced the binding by 95% in C1249 and by 90% in C1269.

About 65 μg of IL-23 was mixed with 75 μg of C1249, C1269, mouse IgG, respectively, and incubated for overnight at 4° C. overnight. The antigen-antibody complex was transferred into digestion buffer using a 100,000 NMWL filter unit. Then, 4 μg of trypsin (0.16 units) in digestion buffer was added and incubated for 2 hours at 37° C. After digestion, Protein G beads were added to capture antibody and fragments bound by antibody. Then, the protein G beads were washed once with PBS and twice with 50 mM Ammonium Bicarbonate, and the captured complexes were eluted with 30 μl of elution buffer (10% Acetonitrile, 0.5% Trifluoracetic Acid).

Eluents of the trypsin-digest complex were desalted by pipetting the sample through ZipTip C18, washed with 0.1% TFA in water, then eluted in 2 μl of α-cyano matrix (10 mg/ml α-cyano, 0.1% TFA, 50% Acetonitrile in water) and spotted on a MALDI-TOF target. The MALDI-TOF (Voyager-DE™ STR, ABI) was calibrated with Calibration mixture 2 (ABI). Spectra were obtained at laser intensity between 1,500-1,800 units and acquisition mass range 800-5,000 m/z.

MSD high bind plates (Meso Scale Diagnostics, Gaithersburg, Md.) were coated, at 4° C. overnight, with 5 ηl of serially diluted samples, from 100 to 0 μg/ml, of different protein reagents, including human IL-23, murine IL-23 and two segment-swapped mutant proteins, 3220 and 3397. One-hundred and fifty μl of 5% MSD Blocker A buffer was added to each well and incubated for 1 hr at room temperature. Plates were washed three times with 0.1 M HEPES buffer, pH 7.4. These protein-charged ELISA micro-wells were incubated with 25 μl of 2 μg/mL MSD Sulfo-TAG labeled C1249, C1269, or CNTO 209 mAbs. After incubation for 2 hours with shaking at room temperature, plates were washed 3 times with 0.1 M HEPES buffer (pH 7.4). MSD Read Buffer T was diluted with distilled water (4 fold) and dispensed at a volume of 150 μl/well and analyzed with a SECTOR imager 6000.

IL-23 Structural Analysis

FIG. 6 shows the structural model for human IL-23 based upon the crystal structure of human IL-12 (pdb code 1f45). It is clear that residues (H75, 179, E82, K83 and G86) are surface exposed and clustered together. This arrangement is typical of conformational epitopes for antibody binding. Therefore, this segment ($_{74}$IHQGLIFYEKLLG$_{86}$) may constitute part of the binding epitope for C1249 as well as species specificity determinants of the epitope. Typical Ab/Ag binding buries approximately 1000 $Å^2$ of surface area. This suggests that additional exposed residues of the IL-23p19 in the vicinity of the above segment would also be required for a typical binding site. Inspection of the molecular model suggests that residues from the neighboring C helix (residues L109, L110, S113, Q114, L116, and Q117) are exposed and would form an extended surface cluster together with the residues in the 74-86 segment. Residues identified and proposed to be part of the epitope for C1249 are labeled and shown in stick models in FIG. 6. The p40 subunit is labeled 2 and the p19 subunit labeled 1.

The sequence for this part of the C helix is identical between human and murine p19. It is plausible that as part of the epitope these residues would contribute to the residual binding of the human-to-murine swap mutants described above. Therefore, the epitope may be comprised of two segments of p19 (74-85 and 108-118) with the exposed residues (H75, 179, E82, K83, G86, L109, L110, S113, Q114, L116, and Q117) to be most likely involved in direct antibody interactions.

Mutagenesis analysis is performed with the IL-23p19 segment spanning residues 108-118 in which the residues are selectively changed individually and/or in groups (i.e., multiple changes). IL-23 activity is monitored after the mutations are made as in the experiments above using the IL-23p19 segment spanning amino acid residues 74-86. The epitope is confirmed based on the change in activity correlated with the various combinations of mutations.

For the purposes of this invention, 70-100% amino acid or nucleotide sequence identity (i.e., 90, 91, 92, 93, 94, 95, 96, 97, 98, 99, 100 or any range or value therein) is determined using a suitable computer algorithm, as known in the art.

It will be clear that the invention can be practiced otherwise than as particularly described in the foregoing description and examples. Numerous modifications and variations of the present invention are possible in light of the above teachings and, therefore, are within the scope of the appended claims.

Sequence Tables

```
SEQ ID NO: 1 (human IL-23p19 subunit)
Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30
```

```
                Cys Gln Gln Leu Ser Gln Lys Leu Cys Thr Leu Ala Trp Ser Ala His
                                 35                  40                  45

Pro Leu Val Gly His Met Asp Leu Arg Glu Gly Asp Glu Glu Thr
                     50                  55                  60

Thr Asn Asp Val Pro His Ile Gln Cys Gly Asp Cys Asp Pro Gln
                65                  70                  75                  80

Gly Leu Arg Asp Asn Ser Gln Phe Cys Leu Gln Arg Ile His Gln Gly
                                 85                  90                  95

Leu Ile Phe Tyr Glu Lys Leu Leu Gly Ser Asp Ile Phe Thr Gly Glu
                                100                 105                 110

Pro Ser Leu Leu Pro Asp Ser Pro Val Ala Gln Leu His Ala Ser Leu
                                115                 120                 125

Leu Gly Leu Ser Gln Leu Leu Gln Pro Glu Gly His His Trp Glu Thr
                            130                 135                 140

Gln Gln Ile Pro Ser Leu Ser Pro Ser Gln Pro Trp Gln Arg Leu Leu
                145                 150                 155                 160

Leu Arg Phe Lys Ile Leu Arg Ser Leu Gln Ala Phe Val Ala Val Ala
                                165                 170                 175

Ala Arg Val Phe Ala His Gly Ala Ala Thr Leu Ser Pro
                            180                 185
```

SEQ ID NO: 2 - C1273 Heavy Chain Nucleotide Sequence
Atgagcagtgaacacagaccccctcaccatgaacttcgggctcagattgattttccttgtccttacttt aaaaggtgtccagtgtgacgtgaacttggtggagtctggggggaggcttagtgaagcctggagggtccc tgaaactctcctgtgcagcctctggattcactttcagtagctataccatgtcttgggttcgccagact ccggagaagaggctggagtgggtcgcaaccattagtagtggtggtacttacacctactatccagacag tgtgaagggccgattcaccatctccagagacaatgccaagaacaccctgtacctgcaaatgagcagtc tgaagtctgaggacacagccatgttttactgtacaagagataaccatgcttacgacaggggccctttc tttgactactggggccaaggcgccactctcacagtctcctca SEQ ID NO: 3 - C1273 Heavy Chain Amino Acid Sequence (CDR
sequences in boldface and underline)
MSSEHRPLTMNFGLRLIFLVLTLKGVQCDVNLVESGGGLVKPGGSLKLSCAASGFTFSSYTMSWVRQT

PEKRLEWVATISSGGTYTYYPDSVKGRFTISRDNAKNTLYLQMSSLKSEDTAMFYCTRDNHAYDRGPF

FDYWGQGATLTVSS

SEQ ID NO: 4 - C1273 Heavy Chain CDR1 Amino Acid Sequence
GFTFSSYTMS

SEQ ID NO: 5 - C1273 Heavy Chain CDR2 Amino Acid Sequence
TISSGGTYTYYPDSVKG

SEQ ID NO: 6 - C1273 Heavy Chain CDR3 Amino Acid Sequence
DNHAYDRGPFFDY

SEQ ID NO: 7 - C1273 Light Chain Nucleotide Sequence
Atggattcacaggcccaggttcttttgttactgctgctatgggtttctggtacctgtggggacattgt gatgtcacagtccccatcctccctagttgtgtcagttggagagaaggttactatgagctgcaagtcca gtcagaacctctttataggagtaatcaaaagaaccacttggcctggtaccagcagaaaccagggcag tctcctacactgctgatttactggacgtccactagggaatctggggtccctgatcgcttcacaggcag tggatctgggacagatttcactctcaccatcagccgtgtgaaggctgaagacctggcagtttattact gtcagcaatattatagctatcctccgacgttcggtggaggcaccaagctggaaatcaaa SEQ ID NO: 8 - C1273 Light Chain Amino Acid Sequence
MDSQAQVLLLLLWVSGTCGDIVMSQSPSSLVVSVGEKVTMSCKSSQNLFYRSNQKNHLAWYQQKPGQ

SPTLLIYWTSTRESGVPDRFTGSGSGTDFTLTISRVKAEDLAVYYCQQYYSYPPTFGGGTKLEIK

-continued

SEQ ID NO: 9 - C1273 Light Chain CDR1 Amino Acid Sequence
KSSQNLFYRSNQKNHLA

SEQ ID NO: 10 - C1273 Light Chain CDR2 Amino Acid Sequence
WTSTRES

SEQ ID NO: 11 - C1273 Light Chain CDR3 Amino Acid Sequence
QQYYSYPPT

SEQ ID NO: 12 - C1269 Heavy Chain Nucleotide Sequence
Atgagcagtgaacacagacccctcaccatgaacttcgggctcagattgattttccttgtcctgacttt aaaaggtgtccagtgtgacgtgaacttggtggagtctgggggaggcttagtgaagcctggagggtccc tgaaactctcctgtgcagcctctggattcactttcagtagctataccatgtcttgggttcgccagact ccggagaagaggctggagtgggtcgcaaccattagtagtggtggtacttacacctactatccagacag tgtgaagggccgattcaccatttccagagacaatgccaagaatacattgtatctgcaaatgagcagtc tgaagtctgaggacacagccatcttttattgtacaagagataaccatgcttacgacaggggcccttt c tttgactctggggccaaggcgccactctcacagtctcctca SEQ ID NO: 13 - C1269 Heavy Chain Amino Acid Sequence
MSSEHRPLTMNFGLRLIFLVLTLKGVQCDVNLVESGGGLVKPGGSLKLSCAASGFTFSSYTMSWVRQT

PEKRLEWVATISSGGTYTYYPDSVKGRFTISRDNAKNTLYLQMSSLKSEDTAIFYCTR**DNHAYDRGPF

FDS**WGQGATLTVSS

SEQ ID NO: 14 - C1269 Heavy Chain CDR1 Amino Acid Sequence
GFTFSSYTMS

SEQ ID NO: 15 - C1269 Heavy Chain CDR2 Amino Acid Sequence
ISSGGTYTYYPDSVKG

SEQ ID NO: 16 - C1269 Heavy Chain CDR3 Amino Acid Sequence
DNHAYDRGPFFDS

SEQ ID NO: 17 - C1269 Light Chain Nucleotide Sequence
Atggattcacaggcccaggttcttatgttactgctgctatgggtttctggtacctgtggggacattgt gatgtcacagtctccatcctccctagctgtgtcagttggagagaaggttactatgagctgcaagtcca gtcagaaccttctttataggaataatcaaaagaactacttggcctggtaccagcagaaaccagggcag tctcctacactgctgatttactggacgtccactagggagtctggggtccctgatcgcttcacaggcag tggatctgggacagatttcactctcaccatcagccgtgtgaaggctgaagacctggcagtttattact gtcagcaatattatagctatcctccgacgttcggtggaggcaccaagctggaaatcaaa SEQ ID NO: 18 - C1269 Light Chain Amino Acid Sequence
MDSQAQVLMLLLLWVSGTCGDIVMSQSPSSLAVSVGEKVTMSCKSSQNLFYRNNQKNYLAWYQQKPGQ

SPTLLIYWTSTRESGVPDRFTGSGSGTDFTLTISRVKAEDLAVYYCQQYYSYPPTFGGGTKLEIK

SEQ ID NO: 19 - C1269 Light Chain CDR1 Amino Acid Sequence
KSSQNLFYRNNQKNYLA

SEQ ID NO: 20 - C1269 Light Chain CDR2 Amino Acid Sequence
YWTSTRES

SEQ ID NO: 21 - C1269 Light Chain CDR3 Amino Acid Sequence
QQYYSYPPT

SEQ ID NO: 22 - C1275 Heavy Chain Nucleotide Sequence
Atgtacttgggactgaactgtgtattcatagttttttctcttaaaaggtgtccagagtgaagtgaacct tgaggagtctggaggaggcttggtgcaacctggaagatccatgaaactctcctgtgttgcctctggat tcactttcagtaactactggatgacctgggtccgccagtctccagagaagggggcttgagtggttgct gaaattagattgaaatctaataattatgcaacacattatgcggagtctgtgaaagggaggttcaccat ctcaagagatgattccaaaagtagtgtctacctgcaaatgaacaacttaagagctgaagacactgcca -continued tttattactgtaccagggggggggggttacgacgtaggagcctggtttgcttactggggccaagggact ctggtcactgtctctgca SEQ ID NO: 23 - C1275 Heavy Chain Amino Acid Sequence
MYLGLNCVFIVFLLKGVQSEVNLEESGGGLVQPGRSMKLSCVASGFTFSNYWMTWVRQSPEKGLEWVA

EIRLKSNNYATHYAESVKGRFTISRDDSKSSVYLQMNNLRAEDTAIYYCTRGGGYDVGAWFAYWGQGT

LVTVSA

SEQ ID NO: 24 - C1275 Heavy Chain CDR1 Amino Acid Sequence
GFTFSNYWMT

SEQ ID NO: 25 - C1275 Heavy Chain CDR2 Amino Acid Sequence
EIRLKSNNYATHYAESVKG

SEQ ID NO: 26 - C1275 Heavy Chain CDR3 Amino Acid Sequence
GGGYDVGAWFAY

SEQ ID NO: 27 - C1275 Light Chain Nucleotide Sequence
Atggagtcagacacactcctgctatgggtgctgctgctctgggttccaggctccactggtgacattgt gctcacccaatctccagcttctttggctgtgtctctagggcagagagccaccatctcctgcagagcca gtgaaaatgttgaatattatggcacaggtttaattcagtggtaccaacagaaaccaggacagccaccc aaactcctcatctatgcttcatccaacgtagaatctggggtccctgccaggtttagtggcagtgggtc tgggacagacttcagcctctacatccatcctgtggaggaggatgatattgcaatgtatttctgtcagc aaagtaggaaggttccttcgacgttcggtggaggcaccaagctggaaatcaaa SEQ ID NO: 28 - C1275 Light Chain Amino Acid Sequence
MESDTLLLWVLLLWVPGSTGDIVLTQSPASLAVSLGQRATISCRASENVEYYGTLIQWYQQKPGQPP

KLLIYASSNVESGVPARFSGSGSGTDFSLYIHPVEEDDIAMYFCQQSRKVPSTFGGGTKLEIK

SEQ ID NO: 29 - C1275 Light Chain CDR1 Amino Acid Sequence
RASENVEYYGTLIQ

SEQ ID NO: 30 - C1275 Light Chain CDR2 Amino Acid Sequence
ASSNVES

SEQ ID NO: 31 - C1275 Light Chain CDR3 Amino Acid Sequence
QQSRKVPST

SEQ ID NO: 32 - C1249 Heavy Chain Nucleotide Sequence
Atggtgttggggctgaagtgggttttctttgttgttttttatcaaggtgtgcattgtgaggtgcaact tgttgagtctggtggaggattggtgcagcctaaaggatcattgaaactctcatgtgccgcctctggtt tcaacttcaataccctatgccatgcactgggtctgccaggctccaggaaagggtttggaatggattggt cgcataagaagtaaaagtcataattatgcaacagactatgccgatccagtgaaagacagattcaccat ctccagagatgattcacaaggcttgctctatctgctaatgaacaacctgaaaactgaggacacagcca tgtattactgtatgagggagggaatctatggtagttttgcttactggggccaagggactctggtcact gtctctgca SEQ ID NO: 33 - C1249 Heavy Chain Amino Acid Sequence
MVLGLKWVFFVVFYQGVHCEVQLVESGGGLVQPKGSLKLSCAASGFNFNTYAMHWVCQAPGKGLEWIG

RIRSKSHNYATDYADPVKDRFTISRDDSQGLLYLLMNNLKTEDTAMYYCMREGIYGSFAYWGQTLVT

VSA

SEQ ID NO: 34 - C1249 Heavy Chain CDR1 Amino Acid Sequence
GFNFNTYAMH

SEQ ID NO: 35 - C1249 Heavy Chain CDR2 Amino Acid Sequence
IRSKSHNYATDYADPVKD

SEQ ID NO: 36 - C1249 Heavy Chain CDR3 Amino Acid Sequence
EGIYGSFAY

-continued

SEQ ID NO: 37 - C1249 Light Chain Nucleotide Sequence
Atggagacagacacactcctgttatgggtactgctgctctggttccaggttccactggtgacattgt gctgacacagtctcctgcttccttagctgtatctctggggcagagggccaccatctcatgcagggcca gcaaaagtgtcagttcatctgcctatagttttttccactggtaccaacagaagccaggacagccaccc aaactcctcatctatcttgcatccaacctacaatctggggtccctgccaggttcagtggcagtgggtc tgggacagacttcaccctcaacatccatcctgtggaggcggaggatgctgcaacctattactgtcaac acagtggggagcttccattcacgttcggctcggggacaaagttggaaataaaa SEQ ID NO: 38 - C1249 Light Chain Amino Acid Sequence
METDTLLLWVLLLWVPGSTGDIVLTQSPASLAVSLGQRATISCRASKSVSSSAYSFFHWYQQKPGQPPKL

LIYLASNLQSGVPARFSGSGSGTDFTLNIHPVEAEDAATYYCQHSGELPFTFGSGTKLEIK

SEQ ID NO: 39 - C1249 Light Chain CDR1 Amino Acid Sequence
CRASKSVSSSAYSFFH

SEQ ID NO: 40 - C1249 Light Chain Amino Acid Sequence
LASNLQS

SEQ ID NO: 41 - C1249 Light Chain Amino Acid Sequence
CQHSGELPFT

---

What is claimed is:

1. An isolated nucleic acid molecule encoding an IL-23p19 antibody capable of binding to human IL-23p19 at one or more regions of human IL-23p19 consisting of the amino acid residues selected from the group consisting of residues 93-102, 93-110, and 127-137 of SEQ ID NO:1.

2. An isolated nucleic acid vector comprising the isolated nucleic acid molecule of claim 1.

3. An isolated host cell comprising the isolated nucleic acid molecule of claim 1, wherein the host cell is prokaryotic or eukaryotic.

4. The isolated host cell of claim 3, wherein said host cell is at least one selected from COS-1, COS-7, HEK293, BHK21, CHO, BSC-1, Hep G2, 653, SP2/0, 293, HeLa, myeloma, and lymphoma cells.

5. A method for producing an IL-23p19 antibody, culturing the isolated host cell of claim 4 under conditions such that the IL-23p19 antibody is expressed and recovered.

6. The isolated nucleic acid of claim 1, wherein said antibody is selected from the group consisting of rodent, chimeric, humanized, and human.

7. An isolated nucleic acid molecule encoding an IL-23p19 antibody that competitively binds to IL-23p19 with the isolated IL-23p19 antibody encoded by the nucleic acid molecule of claim 1.

8. An isolated nucleic acid molecule encoding an IL-23p19 antibody, comprising at least one light chain variable region and at least one heavy chain variable region, said light chain variable region nucleotide sequence comprising:

(a) a complementarity determining region light chain 1 (CDRL1) nucleotide sequence encoding the amino acid sequence of SEQ ID NO:9;
(b) a CDRL2 nucleotide sequence encoding the amino acid sequence of SEQ ID NO:10; and
(c) a CDRL3 nucleotide sequence encoding the amino acid sequence of SEQ ID NO:11,
and said heavy chain variable region nucleotide sequence comprising:
(d) a complementarity determining region heavy chain 1 (CDRH1) nucleotide sequence encoding the amino acid sequence of SEQ ID NO:4;
(e) a CDRH2 nucleotide sequence encoding the amino acid sequence of SEQ ID NO:5; and
(f) a CDRH3 nucleotide sequence encoding the amino acid sequence of SEQ ID NO:6.

9. The isolated nucleic acid molecule of claim 8, comprising a nucleotide sequence encoding the light chain variable region amino acid sequence of SEQ ID NO:8.

10. The isolated nucleic acid molecule of claim 8, comprising a nucleotide sequence encoding the heavy chain variable region amino acid sequence of SEQ ID NO:3.

11. An isolated nucleic acid molecule, comprising the nucleotide sequence of claim 9 and a nucleotide sequence encoding the heavy chain variable amino acid sequence of SEQ ID NO:3.

12. An isolated nucleic acid molecule encoding an IL-23p19 antibody that competitively binds to IL-23p19 with the isolated IL-23p19 antibody encoded by the nucleic acid molecule of claim 11.

* * * * *